(12) United States Patent
Linz et al.

(10) Patent No.: US 8,138,373 B2
(45) Date of Patent: Mar. 20, 2012

(54) PROCESS FOR THE MANUFACTURE OF DIHYDROPTERIDINONES

(75) Inventors: Guenter Linz, Mittelbiberach (DE); Gerd Kraemer, Eberhardzell (DE); Ludwig Gutschera, Ulm (DE); Geert Asche, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/793,970

(22) Filed: Jun. 4, 2010

(65) Prior Publication Data

US 2010/0249458 A1  Sep. 30, 2010

Related U.S. Application Data

(62) Division of application No. 11/197,289, filed on Aug. 4, 2005, now Pat. No. 7,759,485.

(30) Foreign Application Priority Data

Aug. 14, 2004 (EP) .................... 04019365
Jan. 27, 2005 (EP) .................... 05001611

(51) Int. Cl.
C07C 233/74 (2006.01)
(52) U.S. Cl. .................... 564/166
(58) Field of Classification Search .................... 564/166
See application file for complete search history.

(56) References Cited

U.S. PATENT DOCUMENTS

| | | | |
|---|---|---|---|
| 4,957,922 A | 9/1990 | Lammens et al. | |
| 5,043,270 A | 8/1991 | Abrams et al. | |
| 5,167,949 A | 12/1992 | Ferrand et al. | |
| 5,198,547 A | 3/1993 | Bailey et al. | |
| 5,424,311 A | 6/1995 | Billhardt-Troughton et al. | |
| 5,698,556 A | 12/1997 | Chan | |
| 6,096,924 A | 8/2000 | Studer et al. | |
| 6,156,766 A | 12/2000 | Arita et al. | |
| 6,174,895 B1 | 1/2001 | Kleinman | |
| 6,444,677 B2 | 9/2002 | Ikeda et al. | |
| 6,605,255 B2 | 8/2003 | Kroll et al. | |
| 6,806,272 B2 | 10/2004 | Bauer et al. | |
| 6,861,422 B2 | 3/2005 | Hoffmann et al. | |
| 6,875,868 B2 | 4/2005 | Bonnert et al. | |
| 7,238,807 B2 | 7/2007 | Duran et al. | |
| 7,241,889 B2 | 7/2007 | Hoffmann et al. | |
| 7,332,491 B2 | 2/2008 | Grauert et al. | |
| 7,371,753 B2 | 5/2008 | Stadtmueller et al. | |
| 7,414,053 B2 | 8/2008 | Grauert et al. | |
| 7,439,358 B2 | 10/2008 | Linz et al. | |
| 7,547,780 B2 | 6/2009 | Grauert et al. | |
| 7,625,899 B2 | 12/2009 | Hoffmann et al. | |
| 7,626,019 B2 | 12/2009 | Duran et al. | |
| 7,629,460 B2 | 12/2009 | Grauert et al. | |
| 7,700,769 B2 | 4/2010 | Grauert et al. | |
| 7,723,517 B2 | 5/2010 | Grauert et al. | |
| 7,728,134 B2 | 6/2010 | Linz et al. | |
| 7,750,152 B2 | 7/2010 | Hoffman et al. | |
| 7,759,347 B2 | 7/2010 | Hoffmann | |
| 7,759,485 B2 | 7/2010 | Linz et al. | |
| 7,807,831 B2 | 10/2010 | Grauert et al. | |
| 7,816,530 B2 | 10/2010 | Grauert | |
| 2002/0183292 A1 | 12/2002 | Pairet et al. | |
| 2002/0183293 A1 | 12/2002 | Banerjee et al. | |
| 2003/0130286 A1 | 7/2003 | Denny et al. | |
| 2004/0029885 A1 | 2/2004 | Bauer et al. | |
| 2004/0147524 A1 | 7/2004 | Bauer et al. | |
| 2004/0176380 A1 | 9/2004 | Hoffmann et al. | |
| 2005/0014760 A1 | 1/2005 | Hoffmann et al. | |
| 2005/0014761 A1 | 1/2005 | Hoffmann et al. | |
| 2005/0148501 A1 | 7/2005 | Palmer et al. | |
| 2005/0159414 A1 | 7/2005 | Nickolaus et al. | |

(Continued)

FOREIGN PATENT DOCUMENTS

| | | |
|---|---|---|
| CA | 2458699 A1 | 3/2003 |
| CA | 2517020 A1 | 9/2004 |
| CA | 2517010 A1 | 11/2004 |
| CA | 2576290 A1 | 2/2006 |
| EP | 143478 A1 | 6/1985 |
| EP | 347146 A2 | 12/1989 |
| EP | 399856 A1 | 11/1990 |
| EP | 429149 A1 | 5/1991 |

(Continued)

OTHER PUBLICATIONS

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

(Continued)

Primary Examiner — James O Wilson
Assistant Examiner — Cecilia M Jaisle
(74) Attorney, Agent, or Firm — Michael P. Morris; Anthony P. Bottino

(57) ABSTRACT

Disclosed are processes for preparing dihydropteridinones of general formula (I)

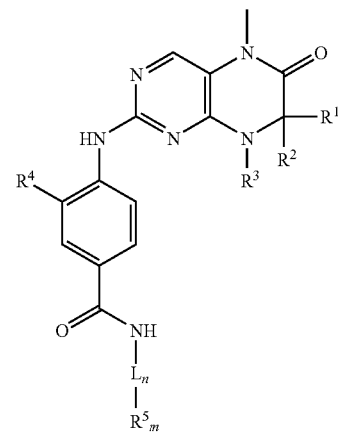

wherein the groups L and $R^1$-$R^5$ have the meanings given in the claims and in the specification.

2 Claims, No Drawings

U.S. PATENT DOCUMENTS

| | | | |
|---|---|---|---|
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0074088 A1 | 4/2006 | Munzert et al. |
| 2006/0079503 A1 | 4/2006 | Schwede et al. |
| 2007/0043055 A1 | 2/2007 | Maier et al. |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0029990 A1 | 1/2009 | Maier et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2010/0029642 A1 | 2/2010 | Hoffmann et al. |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |

FOREIGN PATENT DOCUMENTS

| | | |
|---|---|---|
| ES | 2287583 | 12/2007 |
| RU | 2002125451 A | 1/2004 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 0119825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A1 | 10/2002 |
| WO | 03020722 A1 | 3/2003 |
| WO | 03093249 A1 | 11/2003 |
| WO | 2004014899 A1 | 2/2004 |
| WO | 2004076454 A1 | 9/2004 |
| WO | 2004093848 A2 | 11/2004 |
| WO | 2005067935 A1 | 7/2005 |
| WO | 2006018182 A1 | 2/2006 |
| WO | 2006018185 A2 | 2/2006 |
| WO | 2006018220 A2 | 2/2006 |
| WO | 2006018221 A1 | 2/2006 |
| WO | 2006021378 A1 | 3/2006 |
| WO | 2007014838 A1 | 2/2007 |
| WO | 2007090844 A1 | 8/2007 |
| WO | 2009019205 A1 | 2/2009 |

OTHER PUBLICATIONS

Turner, S., "The Design of Organic Syntheses". Elsevier, 1976, pp. 10 and 149.

Turner, W.W. et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

Viral Defense Foundation. www.viraldefense.org/mission.htm, downloaded Mar. 26, 2009.

Visiting Nurse Association of America. www.vnaa.org/gen/Germ_Protection_Center_Cold_and_Flu_Resources,html, downloaded Mar. 26, 2009.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7,1993, pp. 514-518.

Webster's Comprehensive Dictionary, 1996, pp. 1013-1014 .

Wikipedia. "Melting Point", Jan. 17, 2007. http://en.wikipedia.org/wiki/Melting_point.

Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.

ACPS Meeting, Background Information. "Scientific considerations of plymorphism in pharmaceutical solids: abbreviated new drug applications". Oct. 2002.

Ahlenius, T. List of cardiovascular disorder/diseases. Ahlenius, Karolinska Institutet. Stockholm, Sweden. Cardiovascular Diseases, p. 1-34, Apr. 2007.

Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.

Arnold, K. "Collaboration to play key role in NCI's future, director says". Journal of the National Cancer Institute, Jun. 5, 2002, pp. 790-792, vol. 94, No. 11.

BBC News/Health, Killer Breast Cancern Therapy Hope, www.newsvote.bbc/co./uk, downloaded Mar. 26, 2009.

Bennett, J.C., et al., "Textbook of Medicine", Part XIV, Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Chen, J.X. et al., "Parallel differentiated recognition of ketones and acetals". Angewandte Chemie Int. Ed, vol. 37, Issue 1/2, p. 91-93, 1998.

Dipolar aprotic solvent. Exhibit A, IUPAC Compendium of Chemical Terminology, 2nd Edition, 1997.

Doerwald, F.Z. Book Wiley-VCH Verlag GmbH & Co. KGaA, "Side reactions in organice synthesis: A Guide to Successful Synthesis Design". 2005.

Eurasian Opinion, Appln no. 2007/00389/28, Maly Slatoustinsky per., d.10, kv.15, 101000 Moscow, Russia, "Evromarkpat", 2007.

Ferrand, G., et al., "Synthesis and potential antiallergic activity of new pteridinones and related compounds". Eur. J. Med. Chem, 31, 1996, pp. 273-280. XP—2246920.

Ghandi, L., et al., "An Open-Label Phase II Trial of the PLK Inhibitor BI 2536 in Patients with Sensitive Relapse Small Cell Lung Cancer". ASCO Meeting 2009.

Giron, G. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

International Search Report for PCT/EP2005/008734. mailed Aug. 25, 2006.
Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.
Jamieson, C. et al., "Application of ReactArray Robotics and Design of Experiments Techniques in Optimisation of Supported Reagent Chemistry". Org. Proc. Res. & Dev., 2002, 6, p. 823-825.
Jaworska, J., et al., "Review of methods for assessing the applicability domains of SARS and QSARS". Sponsor: The European Commission—Joint Research Ctr., Institute for Health and Consumer Protection—ECVAM, Italy, 2004.
Kashima, M. K. et al., "Expression of polo-like kinase (PLK1) in non-Hodgkin's lymphomas". NCBI, PubMed, 2005.
Kimball, S. D. et al., "Cell cycle kinases and checkpoint regulation in cancer". Annual Reports in Medicinal Chemistry, 36, Chapter 14, Copyright 2001, pp. 139-148.
Leukemia & Lymphoma Society—Disease Information-Lymphoma. www.leukemia-lymphoma.org/all_page?item_id-7030, downloaded Mar. 26, 2009.
Leukemia & Lymphoma Society—Disease Information. www.leukemia-lymphoma.org/all_page?item_id-7026, downloaded Mar. 26, 2009.
Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.
Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.
Mayer, SF, et al., "Enzyme-initiated domino (cascase) reactions". Chem. Soc. Rev, 2001, p. 332-339.
MedlinePlus: Bacterial Infections. www.nim.nih.gov/medlineplus/print/bacterialinfections.htm, downloaded Mar. 26, 2009.
MedlinePlus: Viral Infections. www.nim.nih.gov/medlineplus/print/viralinfections.htm, downloaded Mar. 26, 2009.
Merck Manual of Medical Information—Home Edition, Section 17. "Parasitic Infections". Chapter 184, 2003.
Mito, K., et al., "Expression of polo-like kinase (PLK1) in non-Hodgkin's lymphomas". NCBI, PubMed, 2005, Leuk. Lymphoma, 46(2), pp. 251-231.
Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
National Kidney Foundation: Chronic Kidney Disease (CKD). www.kidney.org/kidneydisease/ckd/index.cfm, downloaded Mar. 26, 2009.
Norman, P. "PDE4 inhibitors". Ashley Publications Ltd., Expert Opinions Ther. Patents, 1999, pp. 1101-1118.
Office Action mailed Dec. 10, 2003 for U.S. Appl. No. 10/226,710, filed Aug. 23, 2002.
Office Action mailed Apr. 28, 2004 for U.S. Appl. No. 10/374,876, filed Feb. 26, 2003.
Ohio Dept of Health, "Brain and Other Central Nervous System Cancer in Ohio, 1997-2001". Sep. 2004, pp. 1-4.
Organic Chemistry, Grupo Editorial Iberoamerica, Section 13, 3, pp. 301-302, 1983.
Rylander, P.N. "Hydrgenation Methods". 1985, Chapter 13.
Rylander, P.N. "Hydrgenation Methods". 1985, Chapters 3, 4.
Rylander, P.N. "Hydrgenation Methods". 1985, Chapters 8, 9, 10, 11.
Rylander, P.N. "Hydrgenation Methods". 1985, Chapter 5, 6, 7.
Rylander, P.N., "Hydrogenation Methods". 1985, Chapters 1, 2.
Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.
Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.
Science, vol. 310, Oct. 21, 2005, p. 409, Chemistry: One After Another.
Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.
Souillac, P. et al., "Characterization of delivery systems, differential scanning calorimetry". (In Encyclopedia of Controlled Drug Delivery), 1999, John Wiley & Sons, pp. 212-227.
Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21- pp. 129-133.
Takai, N. et al., "Polo-like kinases (PLKs) and cancer". Oncogene, 2005, 24, pp. 287-291.
Dyson, G, et al. "The Chemistry of Synthetic Drugs". 1964, p. 12-19.
Kummer B, et al., "Combination of Radiation and Polo-like Kinase 1 Inhibition with BI6727 in tumour model A431". Vortrag. 20. Symposium •Experimentelle Strahlentherapie und klinische Strahlenbiologie, Exp. Strahlenther. Klin. Strahlenbiol. 20: 93-96 (2011) (Lecture 20, Symposium Experimental Radiation Therapy and Clinical Radiation Biology.).
Kummer, B. et al., Presentation: "Combination of irradiation and polo-like kinase 1 inhibition with BI 6727 in tumour model A 431". OncoRay—National Centre for Radiation Research in Oncology, Dresden 2011, Experimental Radiotherapy and Clinical Radiobiology.
Mashkovkii, M.D., "Medicaments". Moscow, Novaja Volna, 2001, vol. 1, p. 11.
Mashkovskii, M.D. "Drugs", Handbook for Doctors, 1993, Part I, Ch.1, p. 8.
Mikhailov, I.B., Principles of Rational Pharmacotherapy. Handbook for clinical pharmacology for students of pediatric and medical faculties of medical high schools, St. Petersburg, Russia, "Foliant", 1999, p. 25.
Neidle, S. ed., "Cancer Drug Design and Discovery", Elsevier/Academic Press, 2008, p. 427-431.
Rocha Lima, C.M. et al. "Randomized phase II trial of gemcitabine plus irinotecan or docetaxel uin stage IIIB or stage IV NSCLC" Annals of Oncology, 15(3), p. 410-418, 2004.

PROCESS FOR THE MANUFACTURE OF DIHYDROPTERIDINONES

APPLICATION DATA

This application is a divisional of U.S. Ser. No. 11/197,289 filed Aug. 4, 2005, which claims priority benefit to European Patent Applications EP 04 019 365.8 filed August 14, 2004 and EP 05 001 611.2 filed Jan. 27, 2005. The contents of each of the above are incorporated herein by reference in their entirety.

FIELD OF INVENTION

The invention relates to a process for preparing dihydropteridinones of general formula (I)

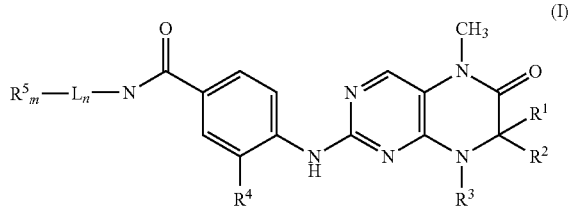

wherein the groups L, $R^1$, $R^2$, $R^3$, $R^4$ and $R^5$ have the meanings given in the claims and specification.

BACKGROUND TO THE INVENTION

Pteridinone derivatives are known from the prior art as active substances with an antiproliferative activity. WO 03/020722 describes the use of dihydropteridinone derivatives for the treatment of tumoral diseases and processes for the preparation thereof.

The aim of the present invention is to provide an improved method of preparing the dihydropteridinones according to the invention.

DETAILED DESCRIPTION OF THE INVENTION

The present invention solves the problem stated above by the method of synthesis described hereinafter which constitutes a convergent process, by comparison with the process described in WO 03/020722.

The invention thus relates to a process for preparing dihydropteridinones of general formula (I)

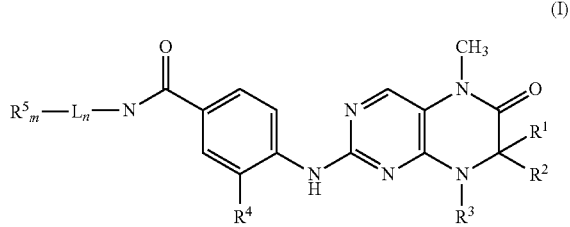

wherein $R^1$, $R^2$ which may be identical or different, denote hydrogen or optionally substituted $C_1$-$C_6$-alkyl, or $R^1$ and $R^2$ together denote a 2- to 5-membered alkyl bridge which may contain 1 to 2 heteroatoms, $R^3$ denotes hydrogen or a group selected from among optionally substituted $C_1$-$C_{12}$-alkyl, $C_2$-$C_{12}$-alkenyl, $C_2$-$C_{12}$-alkynyl and $C_6$-$C_{14}$-aryl, or a group selected from among optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl, $C_3$-$C_{12}$-heterocycloalkyl which contains 1 to 2 heteroatoms, and $C_3$-$C_{12}$-heterocycloalkenyl which contains 1 to 2 heteroatoms, or $R^1$ and $R^3$ or $R^2$ and $R^3$ together denote a saturated or unsaturated $C_3$-$C_4$-alkyl bridge which may optionally contain 1 heteroatom, $R^4$ denotes a group selected from among hydrogen, —CN, hydroxy, —$NR_6R_7$ and halogen, or a group selected from among optionally substituted $C_1$-$C_6$-alkyl, $C_2$-$C_6$-alkenyl, $C_2$-$C_6$-alkynyl, $C_1$-$C_5$-alkyloxy, $C_2$-$C_5$-alkenyloxy, $C_2$-$C_5$-alkynyloxy, $C_1$-$C_6$-alkylthio, $C_1$-$C_6$-alkylsulphoxo and $C_1$-$C_6$-alkylsulphonyl, L denotes a linker selected from among optionally substituted $C_2$-$C_{10}$-alkyl, $C_2$-$C_{10}$-alkenyl, $C_6$-$C_{14}$-aryl, —$C_2$-$C_4$-alkyl-$C_6$-$C_{14}$-aryl, —$C_6$-$C_{14}$-aryl-$C_1$-$C_4$-alkyl, optionally bridged $C_3$-$C_{12}$-cycloalkyl and heteroaryl which optionally contains 1 or 2 nitrogen atoms, n denotes 0 or 1 m denotes 1 or 2

$R^5$ denotes a group selected from among optionally substituted morpholinyl, piperidinyl, piperazinyl, piperazinylcarbonyl, pyrrolidinyl, tropenyl, $R^8$-diketomethylpiperazinyl, sulphoxomorpholinyl, sulphonylmorpholinyl, thiomorpholinyl, —$NR^8R^9$ and azacycloheptyl, $R^6$, $R^7$ which may be identical or different, denote hydrogen or $C_1$-$C_4$-alkyl, and $R^8$, $R^9$ denote unsubstituted nitrogen substituents at $R^5$, which may be identical or different, either hydrogen or a group selected from among $C_1$-$C_6$-alkyl, —$C_1$-$C_4$-alkyl-$C_3$-$C_{10}$-cycloalkyl, $C_3$-$C_{10}$-cycloalkyl, $C_6$-$C_{14}$-aryl, —$C_1$-$C_4$-alkyl-$C_6$-$C_{14}$-aryl, pyranyl, pyridinyl, pyrimidinyl, $C_1$-$C_4$-alkyloxycarbonyl, $C_6$-$C_{14}$-arylcarbonyl, $C_1$-$C_4$-alkylcarbonyl, $C_6$-$C_{14}$-arylmethyloxycarbonyl, $C_6$-$C_{14}$-arylsulphonyl, $C_1$-$C_4$-alkylsulphonyl and $C_6$-$C_{14}$-aryl-$C_1$-$C_4$-alkylsulphonyl, while a compound of formula (II)

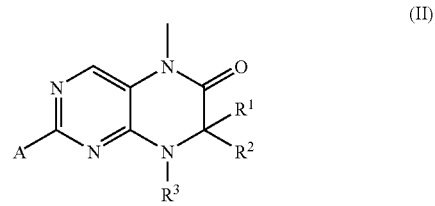

wherein $R^1$ to $R^3$ are defined as specified and A is a leaving group, is reacted with a compound of formula (III),

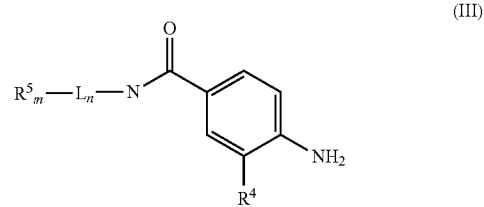

wherein $R^4$, $R^5$, L and m, n may be defined as specified.

The invention further relates to a process for preparing dihydropteridinones of general formula (I) as hereinbefore described, wherein $R_5$ denotes a morpholinyl or piperazinyl group which may be mono or disubstituted by an alkyl or cycloalkyl group, preferably cyclopropylmethyl or dimethyl.

The invention further relates to a process for preparing dihydropteridinones of general formula (I) as hereinbefore described, wherein the dihydropteridinone is selected from among the following dihydropteridinones of general formula (I)

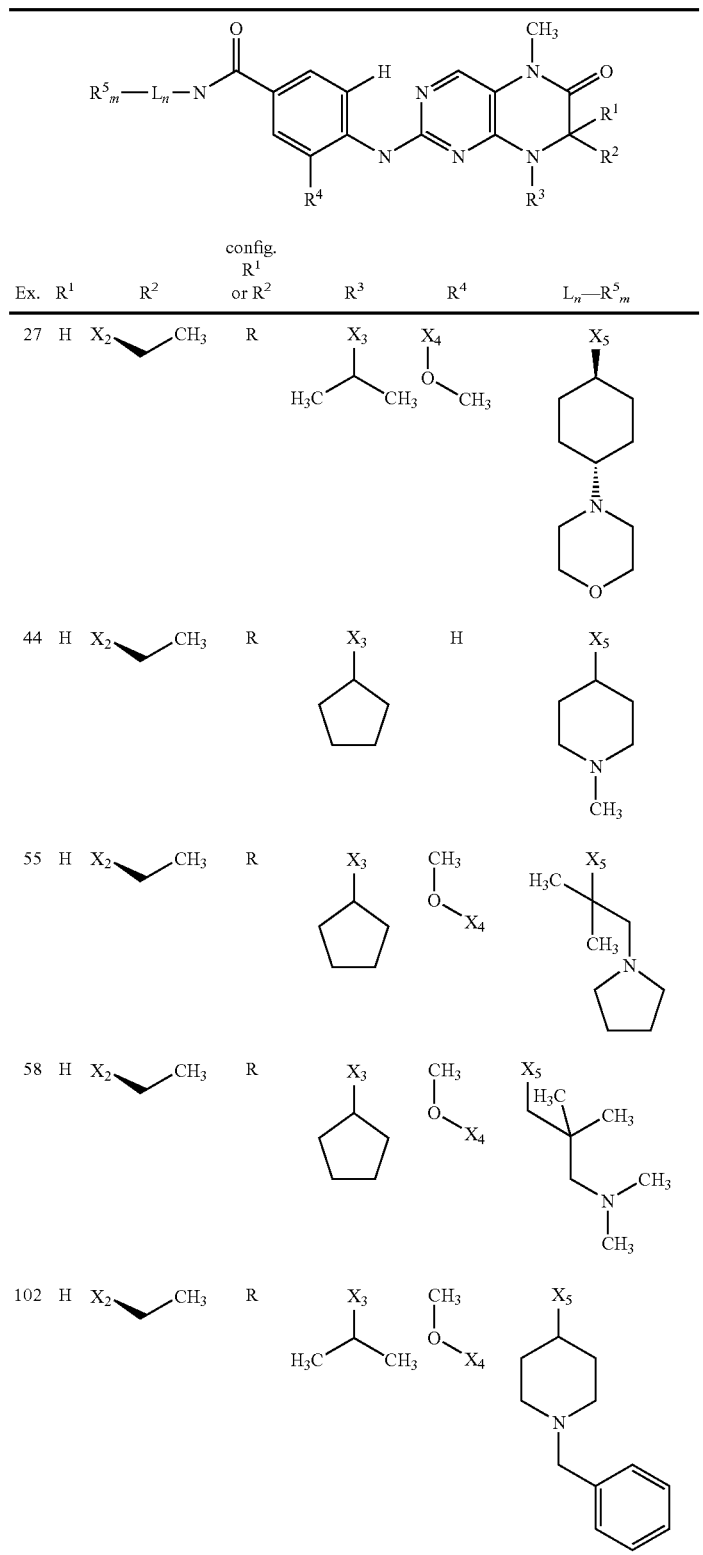

-continued
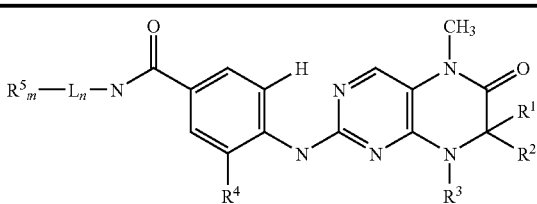
| Ex. | R¹ | R² | config. R¹ or R² | R³ | R⁴ | $L_n$—$R^5_m$ |
|---|---|---|---|---|---|---|
| 103 | H | $X_2$◂CH₃ | R | cyclopentyl-$X_3$ | CH₃-O-$X_4$ | $X_5$-(1-benzylpiperidin-4-yl) |
| 105 | H | $X_2$◂CH₃ | R | cyclopentyl-$X_3$ | $X_4$-O-CH₃ | $X_5$-(trans-cyclohexyl-piperazinyl-CH₂-cyclopropyl) |
| 110 | H | $X_2$—CH₃ | R | (CH₃)₂CH-$X_3$ | $X_4$-O-CH₃ | $X_5$-(trans-cyclohexyl-piperazinyl-CH₂-cyclopropyl) |
| 115 | H | $X_2$◂CH₃ | R | cyclohexyl-$X_3$ | CH₃-O-$X_4$ | $X_5$-(1-benzylpiperidin-4-yl) |

-continued
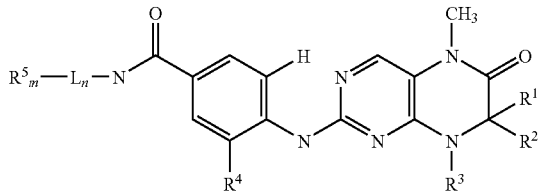
| Ex. | R¹ | R² | config. R¹ or R² | R³ | R⁴ | Lₙ—R⁵ₘ |
|---|---|---|---|---|---|---|
| 133 | H | X₂–CH₃ (ethyl) | R | X₃-cyclopentyl | X₄–O–CH₃ | X₅-cyclohexyl-N-morpholine |
| 134 | H | X₂–CH₃ (ethyl) | R | X₃-cyclopentyl | X₄–O–CH₃ | X₅-cyclohexyl-N-piperazine-N-phenyl |
| 234 | H | X₂–CH₃ (ethyl) | R | X₃-isopropyl | X₄–O–CH₃ | X₅-cyclohexyl-N-(2,6-dimethylmorpholine) |
| 240 | H | X₂–CH₃ | R | X₃-cyclohexyl | CH₃–O–X₄ | X₅-C(CH₃)₂-CH₂-N(CH₃)₂ | while the abbreviations $X_1$, $X_2$, $X_3$, $X_4$ and $X_5$ used in the Table in each case denote a link to a position in the general formula listed in the Table instead of the corresponding groups $R^1$, $R^2$, $R^3$, $R^4$ and L-$R^5$.

In a preferred process the reaction is carried out in the presence of acid catalysts, such as inorganic and organic acids.

Also preferred is a process wherein the acid catalysts used are organic sulphonic acids, preferably methanesulphonic acid, ethanesulphonic acid, ethane-1,2-disulphonic acid, benzenesulphonic acid or p-toluenesulphonic acid.

Particularly preferred is a process wherein the amount of acid catalyst added is between 0.001 and 2 equivalents.

If the compound of formula (I) contains one or more basic groups in the $R^5_m$-$L_n$, group, a further equivalent of acid or correspondingly more equivalents of acid have to be added in addition to the catalytic amount of acid for the purpose of protonation and hence blocking of the basic group or groups. In this case in a particularly preferred process the amount of added acid catalyst is more than one equivalent.

Also particularly preferred is a process wherein the reaction is carried out in a solvent selected from among amides, such as dimethylformamide, dimethylacetamide or N-methylpyrrolidinone, ureas such as 1,3-dimethyl-3,4,5,6-tetrahydro-2(1H)-pyrimidone (DMPU or dimethylpropylurea), sulphoxides such as dimethylsulphoxide or sulphones such as sulpholane, primary alcohols such as methanol, ethanol, 1-propanol, 1-butanol or 1-pentanol, secondary alcohols such as 2-propanol or 2-butanol, isomeric secondary alcohols of pentane or hexane, tertiary alcohols of butane, pentane or hexane, acetonitrile and 2-propylnitrile. Particularly preferred are secondary alcohols such as 2-propanol, 2-butanol or 2-methyl-4-pentanol.

Particularly preferred is a process wherein the reaction temperature is from 18° C. to 180° C., preferably from 100° C. to 150° C.

The reactions may also be carried out under pressure in low-boiling solvents or using microwaves as the energy source.

The reactions are worked up by conventional methods, e.g. by extractive purification steps or precipitation and crystallisation processes.

The compounds according to the invention may be present in the form of the individual optical isomers, mixtures of the individual enantiomers, diastereomers or racemates, in the form of the tautomers and also in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic or methanesulphonic acid.

The term alkyl groups, including alkyl groups which are a part of other groups, denotes branched and unbranched alkyl groups with 1 to 12 carbon atoms, preferably 1-6, most preferably 1-4 carbon atoms, such as, for example: methyl, ethyl, propyl, butyl, pentyl, hexyl, heptyl, octyl, nonyl, decyl and dodecyl. Unless otherwise stated, the abovementioned terms propyl, butyl, pentyl, hexyl, heptyl, octyl, nonyl, decyl and dodecyl include all the possible isomeric forms. For example, the term propyl includes the two isomeric groups n-propyl and iso-propyl, the term butyl includes n-butyl, iso-butyl, sec. butyl and tert.-butyl, the term pentyl includes iso-pentyl and neopentyl.

In the abovementioned alkyl groups one or more hydrogen atoms may optionally be replaced by other groups. For example these alkyl groups may be substituted by fluorine. All the hydrogen atoms of the alkyl group may optionally also be replaced.

The term alkyl bridge, unless otherwise stated, denotes branched and unbranched alkyl groups with 1 to 5 carbon atoms, for example methylene, ethylene, propylene, isopropylene, n-butylene, iso-butyl, sec. butyl and tert.-butyl etc. bridges. Methylene, ethylene, propylene and butylene bridges are particularly preferred. In the alkyl bridges mentioned 1 to 2 C-atoms may optionally be replaced by one or more heteroatoms selected from among oxygen, nitrogen or sulphur.

The term alkenyl groups (including those which are a part of other groups) denotes branched and unbranched alkylene groups with 2 to 10 carbon atoms, preferably 2 to 6 carbon atoms, most preferably 2-3 carbon atoms, provided that they have at least one double bond. Examples include: ethenyl, propenyl, butenyl, pentenyl etc. Unless otherwise stated, the abovementioned terms propenyl, butenyl, etc also include all the possible isomeric forms. For example, the term butenyl includes 1-butenyl, 2-butenyl, 3-butenyl, 1-methyl-1-propenyl, 1-methyl-2-propenyl, 2-methyl-1-propenyl, 2-methyl-2-propenyl and 1-ethyl-1-ethenyl.

In the abovementioned alkenyl groups, unless otherwise stated, one or more hydrogen atoms may optionally be replaced by other groups. For example, these alkyl groups may be substituted by the halogen atoms fluorine. All the hydrogen atoms of the alkenyl group may optionally also be replaced.

The term alkynyl groups (including those which are a part of other groups) denotes branched and unbranched alkynyl groups with 2 to 10 carbon atoms, provided that they have at least one triple bond, for example ethynyl, propargyl, butynyl, pentynyl, hexynyl etc., preferably ethynyl or propynyl.

In the abovementioned alkynyl groups, unless otherwise stated, one or more hydrogen atoms may optionally be replaced by other groups. For example, these alkynyl groups may be substituted by fluorine. All the hydrogen atoms of the alkynyl group may optionally also be replaced.

The term aryl denotes an aromatic ring system with 6 to 14 carbon atoms, preferably 6 or 10 carbon atoms, preferably phenyl, which, unless otherwise stated, may carry one or more of the following substituents, for example: OH, $NO_2$, CN, OMe, —$OCHF_2$, —$OCF_3$, —$NH_2$, halogen, preferably fluorine or chlorine, $C_1$-$C_{10}$-alkyl, preferably $C_1$-$C_5$-alkyl, preferably $C_1$-$C_3$-alkyl, particularly preferably methyl or ethyl, —O—$C_1$-$C_3$-alkyl, preferably —O-methyl or —O-ethyl, —COOH, —COO—$C_1$-$C_4$-alkyl, preferably —O-methyl or —O-ethyl, or —$CONH_2$.

Examples of heteroaryl groups wherein up to two C atoms are replaced by one or two nitrogen atoms include pyrrole, pyrazole, imidazole, triazole, pyridine, pyrimidine, while each of the above-mentioned heteroaryl rings may optionally also be anellated to a benzene ring, preferably benzimidazole, and these heterocycles, unless stated to the contrary, may for example carry one or more of the following substituents: F, Cl, Br, OH, OMe, methyl, ethyl, CN, $CONH_2$, $NH_2$, optionally substituted phenyl, optionally substituted heteroaryl, preferably optionally substituted pyridyl.

Examples of cycloalkyl groups are cycloalkyl groups with 3-12 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally also carry one or more substituents, for example: OH, $NO_2$, CN, OMe, —$OCHF_2$, —$OCF_3$, —$NH_2$ or halogen, preferably fluorine or chlorine, $C_1$-$C_{10}$-alkyl, preferably $C_1$-$C_5$-alkyl, preferably $C_1$-$C_3$-alkyl, particularly preferably methyl or ethyl, —O—$C_1$-$C_3$-alkyl, preferably —O-methyl or —O-ethyl, —COOH, —COO—$C_1$-$C_4$-alkyl, preferably —COO-methyl or —COO-ethyl or —CONH$_2$. Particularly preferred substituents of the cycloalkyl groups are =O, OH, NH$_2$, methyl or F.

Examples of cycloalkenyl groups are cycloalkyl groups with 3-12 carbon atoms which have at least one double bond, for example cyclopropenyl, cyclobutenyl, cyclopentenyl, cyclohexenyl or cycloheptenyl, preferably cyclopropenyl, cyclopententyl or cyclohexenyl, while each of the above-mentioned cycloalkenyl groups may optionally also carry one or more substituents.

"=O" denotes an oxygen atom linked by a double bond.

Examples of heterocycloalkyl groups, unless otherwise stated in the definitions, are 3- to 12-membered, preferably 5-, 6- or 7-membered, saturated or unsaturated heterocycles, which may contain as heteroatoms nitrogen, oxygen or sulphur, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole, pyrazolidine, preferably morpholine, pyrrolidine, piperidine or piperazine, while the heterocyclic group may optionally carry substituents, for example $C_1$-$C_4$-alkyl, preferably methyl, ethyl or propyl.

Examples of polycycloalkyl groups are optionally substituted, bi-, tri-, tetra- or pentacyclic cycloalkyl groups, for example pinane, 2.2.2-octane, 2.2.1-heptane or adamantane. Examples of polycycloalkenyl groups are optionally bridged and/or substituted, 8-membered bi-, tri-, tetra- or pentacyclic cycloalkenyl groups, preferably bicycloalkenyl or tricycloalkenyl groups, if they contain at least one double bond, for example norbornene. Examples of spiroalkyl groups are optionally substituted spirocyclic $C_5$-$C_{12}$ alkyl groups.

The term halogen generally denotes fluorine, chlorine, bromine or iodine, preferably fluorine, chlorine or bromine, particularly preferably chlorine.

The leaving group A denotes a leaving group such as for example fluorine, chlorine, bromine, iodine, methanesulphonyl, ethanesulphonyl, trifluoromethanesulphonyl or p-toluenesulphonyl, preferably chlorine.

The intermediate compounds (II) and (III) may be prepared by methods known from the literature, for example analogously to the methods of synthesis described in WO 03/020722.

The intermediate compound (III) may be prepared by the methods described hereinafter, in the case of trans-diamino-substituted cyclohexanes.

The compounds of formula (I) listed in Table 1, inter alia, are obtained analogously to the method described hereinbefore.

The abbreviations $X_1$, $X_2$, $X_3$, $X_4$ and $X_5$ used in Table 1 each denote a link to a position in the general formula shown under Table 1 instead of the corresponding groups $R^1$, $R^2$, $R^3$, $R^4$ and $L_n$-$R^5_m$.

TABLE 1

| Example No. | $R^1$ | $R^2$ | config. $R^1$ or $R^2$ | $R^3$ | $R^4$ | $L_n$—$R^5_m$ |
|---|---|---|---|---|---|---|
| 1 | H | 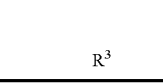 | R | 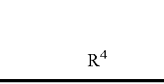 | 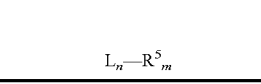 |  |
| 2 | H | 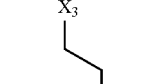 | R | 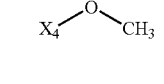 | 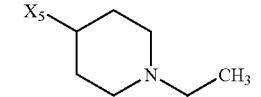 |  |
| 3 | H | 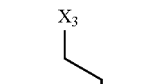 | R | 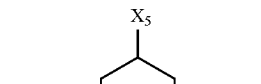 | H |  |

TABLE 1-continued

| Example No. | R¹ | R² | config. R¹ or R² | R³ | R⁴ | Lₙ—R⁵ₘ |
|---|---|---|---|---|---|---|
| 4 | H | X₂—CH₃ | R | X₃—CH₂CH(CH₃)CH₂CH₃ (isopentyl) | H | X₅-(1-ethylpiperidin-4-yl) |
| 5 | H | X₂—CH₃ | R | X₃—CH₂C(CH₃)₃ (neopentyl) | X₄—O—CH₃ | X₅-(1,2,2,6,6-pentamethylpiperidin-4-yl) |
| 6 | H | X₂—CH₃ | R | X₃—CH₂C(CH₃)₃ (neopentyl) | X₄—O—CH₃ | X₅-(1-ethylpiperidin-4-yl) |
| 7 | H | X₂—CH₃ | R | X₃—CH₂C(CH₃)₃ (neopentyl) | X₄—O—CH₃ | X₅-(1-isopropylpiperidin-4-yl) |
| 8 | H | X₂—CH₃ | R | X₃—CH₂C(CH₃)₃ (neopentyl) | H | X₅-(1,2,2,6,6-pentamethylpiperidin-4-yl) |
| 9 | H | X₂—CH₃ | R | X₃—CH₂CH(CH₃)CH₂CH₃ (isopentyl) | X₄—O—CH₃ | X₅-(trans-4-morpholinocyclohexyl) |

TABLE 1-continued

| Example No. | R¹ | R² | config. R¹ or R² | R³ | R⁴ | $L_n$—$R^5_m$ |
|---|---|---|---|---|---|---|
| 10 | H | X₂—CH₃ | R | neopentyl (X₃CH₂C(CH₃)₃) | H | 1-benzylpiperidin-4-yl (X₅) |
| 11 | H | X₂—CH₃ | R | neopentyl | H | 1-ethylpiperidin-4-yl (X₅) |
| 12 | H | X₂—CH₃ | R | neopentyl | H | 1-isopropylpiperidin-4-yl (X₅) |
| 13 | H | X₂—CH₃ | R | cyclopentyl (X₃) | OCH₃ (X₄) | 1-isopropylpiperidin-4-yl (X₅) |
| 14 | H | X₂—CH₃ | R | cyclopentyl (X₃) | H | 1-isopropylpiperidin-4-yl (X₅) |
| 15 | H | X₂—CH₃ | R | cyclopentyl (X₃) | OCH₃ (X₄) | trans-4-(pyrrolidin-1-yl)cyclohexyl (X₅) |

TABLE 1-continued
| Example No. | R¹ | R² | config. R¹ or R² | R³ | R⁴ | L$_n$—R$^5_m$ |
|---|---|---|---|---|---|---|
| 16 | H | X₂◄CH₃ | R | X₃–cyclopentyl | X₄–O–CH₃ | X₅–cyclohexyl–N–piperidine |
| 17 | H | X₂◄CH₃ | R | X₃–cyclopentyl | CH₃–O–X₄ | X₅–(1-ethyl)piperidin-4-yl |
| 18 | H | X₂◄CH₃ | R | X₃–cyclopentyl | H | X₅–(1-ethyl)piperidin-4-yl |
| 19 | H | X₂—CH₂CH₃ | R | X₃–cyclopentyl | X₄–O–CH₃ | X₅–cyclohexyl–N–pyrrolidine |
| 20 | H | X₂◄CH₃ | R | X₃–CH(CH₃)₂ | CH₃–O–X₄ | X₅–(1-ethyl)piperidin-4-yl |

TABLE 1-continued

| Example No. | $R^1$ | $R^2$ | config. $R^1$ or $R^2$ | $R^3$ | $R^4$ | $L_n$—$R^5_m$ |
|---|---|---|---|---|---|---|
| 21 | H | $X_2$—CH$_3$ (ethyl) | R | cyclopentyl ($X_3$) | $CH_3$—O—$X_4$ | 1,2,2,6,6-pentamethylpiperidin-4-yl ($X_5$) |
| 22 | H | $X_2$—CH$_3$ (ethyl) | R | cyclopentyl ($X_3$) | $CH_3$—O—$X_4$ | 1-ethylpiperidin-4-yl ($X_5$) |
| 23 | H | $X_2$—CH$_3$ (ethyl) | R | cyclopentyl ($X_3$) | $CH_3$—O—$X_4$ | 1-isopropylpiperidin-4-yl ($X_5$) |
| 24 | H | $X_2$—CH$_3$ | R | cyclopentyl ($X_3$) | $X_4$—O—CH$_3$ | 4-morpholinocyclohexyl ($X_5$) |
| 25 | H | $X_2$—CH$_3$ | R | cyclopentyl ($X_3$) | $X_4$—O—CH$_3$ | 4-(piperidin-1-yl)cyclohexyl ($X_5$) |

TABLE 1-continued

| Example No. | R¹ | R² | config. R¹ or R² | R³ | R⁴ | Lₙ—R⁵ₘ |
|---|---|---|---|---|---|---|
| 26 | H | X₂—CH₃ (wedge) | R | X₃—CH(CH₃)₂ | X₄—O—CH₃ | X₅—cyclohexyl—N-morpholine |
| 27 | H | X₂—CH₂CH₃ | R | X₃—CH(CH₃)₂ | X₄—O—CH₃ | X₅—cyclohexyl—N-morpholine |
| 28 | H | X₂—CH₂CH₃ | R | X₃—CH(CH₃)₂ | X₄—O—CH₃ | X₅—cyclohexyl—N-morpholine |
| 29 | H | X₂—CH₃ (wedge) | R | X₃—CH₂CH(CH₃)₂ | X₄—O—CH₃ | X₅—cyclohexyl—N-piperidine |
| 30 | H | X₂—CH₃ (wedge) | R | X₃—cyclopentyl | CH₃—O—X₄ | X₅—2,2,6,6-tetramethyl-1-methyl-piperidin-4-yl |

TABLE 1-continued
| Example No. | R¹ | R² | config. R¹ or R² | R³ | R⁴ | $L_n$—$R^5_m$ |
|---|---|---|---|---|---|---|
| 31 | H | 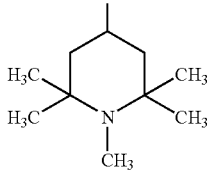 | R | 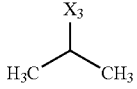 | H |  |
| 32 | H | 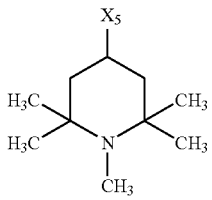 | R | 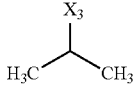 | 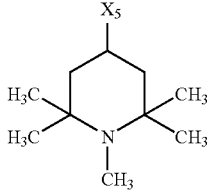 | 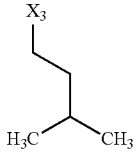 |
| 33 | H |  | R | 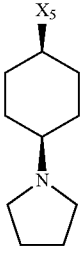 | H | 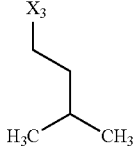 |
| 34 | H | X₂◂CH₃ | R |  | X₄—O—CH₃ | 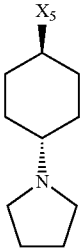 |
| 35 | H | X₂◂CH₃ | R | (same isobutyl-like group) | X₄—O—CH₃ | (same cyclohexyl-pyrrolidine group) |

TABLE 1-continued

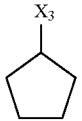

| Example No. | $R^1$ | $R^2$ | config. $R^1$ or $R^2$ | $R^3$ | $R^4$ | $L_n$—$R^5{}_m$ |
|---|---|---|---|---|---|---|
| 36 | H | $X_2$⬛CH$_3$ | R | $X_3$–cyclopentyl | $X_4$–O–CH$_3$ | $X_5$–cyclohexyl–N-pyrrolidinyl |
| 37 | H | $X_2$⬛CH$_3$ | R | $X_3$–CH$_2$CH$_2$CH(CH$_3$)$_2$ | $X_4$–O–CH$_3$ | $X_5$–(3-pyrrolidinyl)–N-ethyl |
| 38 | H | $X_2$⬛CH$_3$ | R | $X_3$–CH$_2$CH$_2$CH(CH$_3$)$_2$ | $X_4$–O–CH$_3$ | $X_5$–cyclohexyl–N-morpholinyl |
| 39 | H | $X_2$⬛CH$_3$ | R | $X_3$–CH$_2$CH$_2$CH(CH$_3$)$_2$ | H | $X_5$–(3-pyrrolidinyl)–N-ethyl |
| 40 | H | $X_2$⬛CH$_3$ | R | $X_3$–cyclopentyl | $X_4$–O–CH$_3$ | $X_5$–cyclohexyl–N-morpholinyl |

TABLE 1-continued

| Example No. | R¹ | R² | config. R¹ or R² | R³ | R⁴ | Lₙ—R⁵ₘ |
|---|---|---|---|---|---|---|
| 41 | H | X₂—CH₃ | R | X₃—phenyl | CH₃—O—X₄ | X₅—(1-methylpiperidin-4-yl) |
| 42 | H | X₂—CH₂CH₃ | R | X₃—CH₂CH(CH₃)₂ (isobutyl) | CH₃—O—X₄ | X₅—(1-methyl-8-azabicyclo) |
| 43 | X₁—CH₃ | X₂—CH₃ | | X₃—CH₂CH(CH₃)₂ | H₃C—O—X₄ | X₅—(1-methyl-8-azabicyclo) |
| 44 | H | X₂—CH₂CH₃ | R | X₃—cyclopentyl | H | X₅—(1-methylpiperidin-4-yl) |
| 45 | H | X₂—CH₂CH₃ | R | X₃—cyclopentyl | H₃C—O—X₄ | X₅—(1-methyl-8-azabicyclo) |
| 46 | H | X₂—CH₂CH₃ | R | X₃—cyclopentyl | H₃C—O—X₄ | X₅—(1-methylpiperidin-4-yl) |

TABLE 1-continued

| Example No. | R¹ | R² | config. R¹ or R² | R³ | R⁴ | Lₙ—R⁵ₘ |
|---|---|---|---|---|---|---|
| 47 | H | X₂—CH₂CH₃ | R | X₃-cyclopentyl | H | X₅-(1-methyl-8-azabicyclo) |
| 48 | H | X₂—CH₃ | R | X₃-phenyl | H | X₅-(1-methylpiperidin-4-yl) |
| 49 | H | X₂—CH₃ | R | X₃-cyclopentyl | CH₃O—X₄ | X₅-C(CH₃)₂CH₂-pyrrolidinyl |
| 50 | H | X₂—CH₃ | R | X₃-CH₂C(CH₃)₃ | X₄—OCH₃ | X₅-C(CH₃)₂CH₂-pyrrolidinyl |
| 51 | H | X₂-cyclopropyl | R | X₃-cyclopentyl | CH₃O—X₄ | X₅-CH₂C(CH₃)₂CH₂N(CH₃)₂ |
| 52 | H | X₂—CH₃ | R | X₃-CH₂C(CH₃)₃ | X₄—OCH₃ | X₅-CH₂C(CH₃)₂CH₂N(CH₃)₂ |

TABLE 1-continued

| Example No. | R¹ | R² | config. R¹ or R² | R³ | R⁴ | Lₙ—R⁵ₘ |
|---|---|---|---|---|---|---|
| 53 | X₁—CH₃ | X₂—CH₃ | | (CH₂)₂CH(CH₃)₂ attached via X₃ | OCH₃ (O—X₄) | X₅—CH₂C(CH₃)₂CH₂—N(CH₃)₂ |
| 54 | H | X₂—CH₂CH₃ | R | CH(CH₃)₂ via X₃ (isobutyl) | OCH₃ | H₃C—C(CH₃)₂—CH₂—pyrrolidinyl (X₅) |
| 55 | H | X₂—CH₂CH₃ | R | cyclopentyl via X₃ | OCH₃ | H₃C—C(CH₃)₂—CH₂—pyrrolidinyl (X₅) |
| 56 | H | X₂—CH₃ | R | CH(CH₃)₂ via X₃ (isobutyl) | OCH₃ | H₃C—C(CH₃)₂—CH₂—pyrrolidinyl (X₅) |
| 57 | H | X₂—CH₂CH₃ | R | CH(CH₃)₂ via X₃ (isobutyl) | OCH₃ | X₅—CH₂C(CH₃)₂CH₂—N(CH₃)₂ |
| 58 | H | X₂—CH₂CH₃ | R | cyclopentyl via X₃ | OCH₃ | X₅—CH₂C(CH₃)₂CH₂—N(CH₃)₂ |

TABLE 1-continued

| Example No. | R¹ | R² | config. R¹ or R² | R³ | R⁴ | Lₙ—R⁵ₘ |
|---|---|---|---|---|---|---|
| 59 | H | X₂—CH₃ | R | X₃-phenyl | H₃C—O—X₄ | X₅-(1-methylpiperidin-4-yl) |
| 60 | H | X₂—CH₃ | R | X₃-cyclopentyl | CH₃—O—X₄ | X₅-CH₂-C(CH₃)₂-CH₂-N(CH₃)₂ |
| 61 | X₁—CH₃ | X₂—CH₃ |  | X₃-CH₂-CH(CH₃)-CH₃ | H₃C—O—X₄ | X₅-(1-methylpiperidin-4-yl) |
| 62 | H | X₂—CH₃ | R | X₃-cyclopentyl | CH₃—O—X₄ | (H₃C-CH₂)₂N-CH₂-CH₂-X₅ |
| 63 | H | X₂—CH₃ | R | X₃-cyclopentyl | CH₃—O—X₄ | morpholino-(CH₂)₃-X₅ |
| 64 | H | X₂—CH₃ | R | X₃-cyclopentyl | CH₃—O—X₄ | piperidino-(CH₂)₃-X₅ |
| 65 | H | X₂—CH₃ | R | X₃-cyclopentyl | CH₃—O—X₄ | morpholino-CH₂-CH₂-X₅ |
| 66 | H | X₂—CH₃ | R | X₃-cyclopentyl | CH₃—O—X₄ | piperidino-CH₂-CH₂-X₅ |

TABLE 1-continued

| Example No. | R¹ | R² | config. R¹ or R² | R³ | R⁴ | $L_n$—$R^5_m$ |
|---|---|---|---|---|---|---|
| 67 | H | X₂—CH₃ | R | X₃-cyclopentyl | CH₃-O-X₄ | (CH₃)(H₃C)N-CH₂CH₂-X₅ |
| 68 | H | X₂—CH₃ | R | X₃-cyclopentyl | H | H₃C-N-bicyclic-X₅ |
| 69 | H | X₂—CH₃ | R | X₃-cyclopentyl | H | morpholine-propyl-X₅ |
| 70 | H | X₂—CH₃ | R | X₃-cyclopentyl | H | piperidine-ethyl-X₅ |
| 71 | H | X₂—CH₃ | R | X₃-CH(CH₃)₂ | H₃C-O-X₄ | X₅-ethyl-morpholine |
| 72 | H | X₂—CH₃ | R | X₃-CH(CH₃)₂ | H₃C-O-X₄ | X₅-ethyl-piperidine |
| 73 | H | X₂—CH₃ | R | X₃-CH(CH₃)₂ | H | X₅-ethyl-N(CH₂CH₃)₂ |
| 74 | H | X₂—CH₃ | R | X₃-CH(CH₃)₂ | H₃C-O-X₄ | X₅-ethyl-N(CH₂CH₃)(CH₂CH₃) |

TABLE 1-continued

| Example No. | R¹ | R² | config. R¹ or R² | R³ | R⁴ | Lₙ—R⁵ₘ |
|---|---|---|---|---|---|---|
| 75 | H | X₂⏋CH₃ | R | cyclopentyl-X₃ | OCH₃, X₄ | H₃C-N(CH₃)-CH₂CH₂CH₂-X₅ |
| 76 | H | X₂⏋CH₃ | R | cyclopentyl-X₃ | OCH₃, X₄ | H₃C-CH₂-N(CH₂CH₃)-CH₂CH₂CH₂-X₅ |
| 77 | H | X₂-CH₂CH₃ | R | CH(CH₃)₂-X₃ | H | X₅-CH₂CH₂-piperidin-1-yl |
| 78 | H | X₂-CH₂CH₃ | R | CH(CH₃)₂-X₃ | H | X₅-CH₂CH₂-morpholin-4-yl |
| 79 | H | X₂⏋CH₃ | R | cyclopentyl-X₃ | H | 1-methylpiperidin-4-yl-X₅ |
| 80 | H | X₂⏋CH₃ | R | cyclopentyl-X₃ | OCH₃, X₄ | 1-methylpiperidin-4-yl-X₅ |
| 81 | H | X₂-cyclopropyl | R | cyclopentyl-X₃ | OCH₃, X₄ | 1-methylpiperidin-4-yl-X₅ |

TABLE 1-continued

| Example No. | R¹ | R² | config. R¹ or R² | R³ | R⁴ | L$_n$—R⁵$_m$ |
|---|---|---|---|---|---|---|
| 82 | H | X₂-cyclopropyl | R | X₃-cyclopentyl | OCH₃—X₄ | X₅-(N-methyl azabicyclic) |
| 83 | H | X₂◂CH₃ | R | X₃-cyclopentyl | H₃C—X₄ | 1-methylpiperidin-4-yl-X₅ |
| 84 | H | X₂◂CH₃ | R | X₃-cyclohexyl | OCH₃—X₄ | 1-methylpiperidin-4-yl-X₅ |
| 85 | H | X₂◂CH₃ | R | X₃-cyclohexyl | H | 1-methylpiperidin-4-yl-X₅ |
| 86 | H | X₂◂CH₃ | R | X₃-cyclohexyl | OCH₃—X₄ | X₅—C(CH₃)(C₂H₅)CH₂N(CH₃)₂ |
| 87 | H | X₂◂CH₃ | R | X₃-cyclohexyl | OCH₃—X₄ | X₅—C(CH₃)₂CH₂-pyrrolidinyl |

TABLE 1-continued

| Example No. | R¹ | R² | config. R¹ or R² | R³ | R⁴ | $L_n$—$R^5_m$ |
|---|---|---|---|---|---|---|
| 88 | H | X₂—CH₃ (ethyl) | R | X₃-phenyl | H₃C—O—X₄ | X₅-(1-methylpiperidin-4-yl) |
| 89 | H | X₂—CH₃ (ethyl) | R | X₃-phenyl | H₃C—O—X₄ | X₅—C(CH₃)₂—CH₂—N(CH₃)₂ |
| 90 | H | X₂—CH₃ (ethyl) | R | X₃—CH₂CH₂—CH(CH₃)₂ | H₃C—O—X₄ | X₅—C(CH₃)₂—CH₂—N(CH₃)₂ |
| 91 | H | X₂—CH₃ | R | X₃-cyclohexyl | H₃C—O—X₄ | X₅-(8-methyl-8-azabicyclo) |
| 92 | H | X₂—CH₃ | R | X₃-cyclohexyl | H | X₅-(8-methyl-8-azabicyclo) |
| 93 | H | X₂-cyclopropyl | R | X₃-cyclopentyl | H | H₃C—N-piperidin-4-yl—X₅ |
| 94 | H | X₂—CH₃ | R | X₃-cyclohexyl | H₃C—X₄ | X₅-(1-methylpiperidin-4-yl) |

TABLE 1-continued

| Example No. | R¹ | R² | config. R¹ or R² | R³ | R⁴ | Lₙ—R⁵ₘ |
|---|---|---|---|---|---|---|
| 95 | H | X₂―CH₃ (wedge) | R | X₃-cyclohexyl | H₃C―X₄ | X₅-N-methyl azabicyclic |
| 96 | H | X₂―CH₃ | R | X₃-cyclohexyl | H₃C―O―X₄ | X₅-(N-methylpiperidin-4-yl) |
| 97 | H | X₂―CH₃ | R | X₃-cyclohexyl | H₃C―O―X₄ | X₅-(4-morpholinocyclohexyl) |
| 98 | H | X₂―CH₃ (wedge) | R | X₃-cyclohexyl | X₄―O―CH₃ | X₅-(4-pyrrolidinylcyclohexyl) |
| 99 | H | X₂―CH₃ | R | X₃-isopropyl | X₄―O―CH₃ | X₅-(4-(4-(cyclopropylmethyl)piperazin-1-yl)cyclohexyl) |

TABLE 1-continued

| Example No. | R¹ | R² | config. R¹ or R² | R³ | R⁴ | $L_n$—$R^5_m$ |
|---|---|---|---|---|---|---|
| 100 | H | X₂—CH₃ | R | isopentyl (H₃C-CH(CH₃)-CH₂-CH₂-X₃) | X₄-O-CH₃ | trans-4-(4-cyclopropylmethyl-piperazin-1-yl)cyclohexyl-X₅ |
| 101 | H | X₂—CH₃ | R | isopropyl (H₃C-CH(CH₃)-X₃) | CH₃-O-X₄ | 1-benzylpiperidin-4-yl-X₅ |
| 102 | H | X₂—CH₂—CH₃ | R | isopropyl (H₃C-CH(CH₃)-X₃) | CH₃-O-X₄ | 1-benzylpiperidin-4-yl-X₅ |
| 103 | H | X₂—CH₃ | R | cyclopentyl-X₃ | CH₃-O-X₄ | 1-benzylpiperidin-4-yl-X₅ |

TABLE 1-continued

| Example No. | R¹ | R² | config. R¹ or R² | R³ | R⁴ | Lₙ—R⁵ₘ |
|---|---|---|---|---|---|---|
| 104 | H | X₂—CH₃ | R | phenyl-X₃ | CH₃—O—X₄ | X₅-(4-piperidinyl) N-benzyl |
| 105 | H | X₂—CH₃ | R | cyclopentyl-X₃ | X₄—O—CH₃ | X₅-cyclohexyl-piperazinyl-CH₂-cyclopropyl |
| 106 | H | X₂—CH₃ | R | cyclopentyl-X₃ | X₄—O—CH₃ | X₅-cyclohexyl-(4-methylpiperazinyl) |
| 107 | H | X₂—CH₃ | R | cyclopentyl-X₃ | X₄—O—CH₃ | X₅-cyclohexyl-piperazinyl-CH₂-cyclopropyl |

TABLE 1-continued

| Example No. | R¹ | R² | config. R¹ or R² | R³ | R⁴ | Lₙ—R⁵ₘ |
|---|---|---|---|---|---|---|
| 108 | H | X₂—CH₃ | R | X₃ CH(CH₃)₂ | CH₃—O—X₄ | X₅-piperidine-tetrahydropyran |
| 109 | H | X₂—CH₃ | R | X₃-cyclopentyl | CH₃—O—X₄ | X₅-piperidine-tetrahydropyran |
| 110 | H | X₂—CH₃ | R | X₃ CH(CH₃)₂ | X₄—O—CH₃ | X₅-cyclohexyl-piperazine-CH₂-cyclopropyl |
| 111 | H | X₂—CH₃ | R | X₃—CH₂—CH(CH₃)₂ | X₄—O—CH₃ | X₅-cyclohexyl-morpholine |

TABLE 1-continued

| Example No. | R¹ | R² | config. R¹ or R² | R³ | R⁴ | Lₙ—R⁵ₘ |
|---|---|---|---|---|---|---|
| 112 | H | X₂—CH₃ | R | X₃ isopropyl | X₄—O—CH₃ | X₅-cyclohexyl-piperazinyl-CH₂-cyclopropyl |
| 113 | H | X₂—CH₂CH₃ | R | X₃ isopropyl | X₄—O—CH₃ | X₅-cyclohexyl-N-methylpiperazinyl |
| 114 | H | X₂—CH₃ | R | X₃-CH₂-CH(CH₃)₂ | X₄—O—CH₃ | X₅-cyclohexyl-N(CH₃)₂ |
| 115 | H | X₂—CH₃ | R | X₃-cyclohexyl | CH₃—O—X₄ | X₅-piperidinyl-N-benzyl |

TABLE 1-continued

| Example No. | R¹ | R² | config. R¹ or R² | R³ | R⁴ | Lₙ—R⁵ₘ |
|---|---|---|---|---|---|---|
| 116 | H | X₂—CH₃ (wedge) | R | cyclopentyl-X₃ | CH₃—O—X₄ | piperidine-X₅ with N-tetrahydropyran-4-yl |
| 117 | H | X₂—CH₃ | R | cyclohexyl-X₃ | CH₃—O—X₄ | 2,2,6,6-tetramethyl-1-methylpiperidin-4-yl-X₅ |
| 118 | H | X₂—CH₃ | R | cyclohexyl-X₃ | CH₃—O—X₄ | 1-isopropylpiperidin-4-yl-X₅ |
| 119 | H | X₂—CH₃ | R | cyclohexyl-X₃ | CH₃—O—X₄ | 1-ethylpiperidin-4-yl-X₅ |
| 120 | H | X₂—CH₃ | R | cyclohexyl-X₃ | CH₃—O—X₄ | 1-(tetrahydropyran-4-yl)piperidin-4-yl-X₅ |

TABLE 1-continued

| Example No. | R¹ | R² | config. R¹ or R² | R³ | R⁴ | Lₙ—R⁵ₘ |
|---|---|---|---|---|---|---|
| 121 | H | X₂—CH₃ | R | X₃-cyclohexyl | CH₃—O—X₄ | X₅-(3R)-1-ethylpyrrolidinyl |
| 122 | H | X₂—CH₃ | R | X₃-cyclohexyl | CH₃—O—X₄ | X₅-(3R)-1-isopropylpyrrolidinyl |
| 123 | H | X₂—CH₃ | R | X₃-cyclohexyl | CH₃—O—X₄ | X₅-(3S)-1-ethylpyrrolidinyl |
| 124 | H | X₂—CH₃ | R | X₃-cyclohexyl | CH₃—O—X₄ | X₅-(3S)-1-isopropylpyrrolidinyl |
| 125 | H | X₂—CH₃ | R | X₃-cyclohexyl | X₄—O—CH₃ | X₅-(4-pyrrolidin-1-yl)cyclohexyl |

TABLE 1-continued
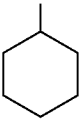
| Example No. | R¹ | R² | config. R¹ or R² | R³ | R⁴ | Lₙ—R⁵ₘ |
|---|---|---|---|---|---|---|
| 126 | H |  | R |  | 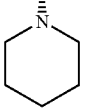 | 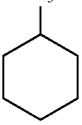 |
| 127 | H | 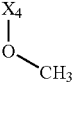 | R |  | 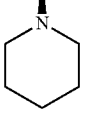 | 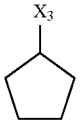 |
| 128 | H | 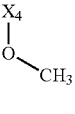 | R | 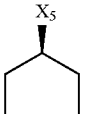 | 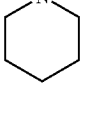 | 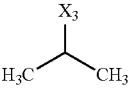 |
| 129 | H | 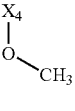 | R | 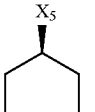 | 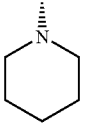 |  |

TABLE 1-continued

| Example No. | R¹ | R² | config. R¹ or R² | R³ | R⁴ | Lₙ—R⁵ₘ |
|---|---|---|---|---|---|---|
| 130 | H | X₂–CH₃ | R | X₃-cyclohexyl | X₄–O–CH₃ | X₅-cyclohexyl-morpholine |
| 131 | H | X₂–CH₃ (ethyl) | R | X₃-cyclopentyl | X₄–O–CH₃ | X₅-cyclohexyl-morpholine |
| 132 | H | X₂–CH₃ (ethyl) | R | X₃-isopropyl | X₄–O–CH₃ | X₅-cyclohexyl-pyrrolidine |
| 133 | H | X₂–CH₃ (ethyl) | R | X₃-cyclopentyl | X₄–O–CH₃ | X₅-cyclohexyl-morpholine |

TABLE 1-continued

| Example No. | R¹ | R² | config. R¹ or R² | R³ | R⁴ | $L_n$—$R^5_m$ |
|---|---|---|---|---|---|---|
| 134 | H | X₂–CH₃ | R | cyclopentyl (X₃) | X₄–O–CH₃ | X₅-cyclohexyl-piperazinyl-phenyl |
| 135 | H | X₂–CH₃ | R | isopropyl (X₃, H₃C–CH–CH₃) | X₄–O–CH₃ | X₅-cyclohexyl-pyrrolidinyl |
| 136 | H | X₂–CH₃ | R | cyclopentyl (X₃) | X₄–O–CH₃ | X₅-cyclohexyl-piperidinyl |
| 137 | H | X₂–CH₃ | R | cyclohexyl (X₃) | X₄–O–CH₃ | X₅-cyclohexyl-morpholinyl |

TABLE 1-continued

| Example No. | R¹ | R² | config. R¹ or R² | R³ | R⁴ | Lₙ—R⁵ₘ |
|---|---|---|---|---|---|---|
| 138 | H | X₂–CH₃ (wedge) | R | cyclopentyl (X₃) | X₄–O–CH₃ | X₅–cyclohexyl–N-pyrrolidinyl |
| 139 | H | X₂–CH₃ | R | CH(CH₃)₂ (X₃) | H₃C–O–X₄ | X₃–(N-methyl azabicyclic) |
| 140 | H | X₂–CH₃ | R | CH(CH₃)₂ (X₃) | H₃C–O–X₄ | X₃–(N-methylpiperidin-4-yl) |
| 141 | H | X₂–CH₃ | R | CH(CH₃)₂ (X₃) | H₃C–O–X₄ | X₅–(CH₂)₃–morpholino |
| 142 | H | X₂–CH₃ | R | CH(CH₃)₂ (X₃) | H₃C–O–X₄ | X₅–(CH₂)₃–piperidino |
| 143 | H | X₂–CH₃ | R | CH(CH₃)₂ (X₃) | H | X₅–(CH₂)₃–morpholino |

TABLE 1-continued

| Example No. | R¹ | R² | config. R¹ or R² | R³ | R⁴ | Lₙ—R⁵ₘ |
|---|---|---|---|---|---|---|
| 144 | H | X₂—CH₃ (wedge) | R | H₃C-CH(X₃)-CH₃ | H | X₅-(1-methylpiperidin-4-yl) |
| 145 | H | H₃C—X₂ (wedge) | R | H₃C-C(CH₃)(CH₃)-CH₂-X₃ | X₄—O—CH₃ | X₅-(1-methylpiperidin-4-yl) |
| 146 | H | X₂—CH₃ (wedge) | R | X₃-CH₂-CH₂-CH(CH₃)-CH₃ | X₄—O—CH₃ | X₅-(1-methylpiperidin-4-yl) |
| 147 | H | H₃C—X₂ (wedge) | R | H₃C-C(CH₃)(CH₃)-CH₂-X₃ | H | X₅-(N-methyl-azabicyclic) |
| 148 | H | X₂—CH₂—CH₃ | R | X₃-CH₂-CH₂-CH(CH₃)-CH₃ | X₄—O—CH₃ | X₅-CH₂-CH₂-piperidin-1-yl |
| 149 | H | X₂—CH₂—CH₃ | R | X₃-CH₂-CH₂-CH(CH₃)-CH₃ | X₄—O—CH₃ | X₃-CH₂-CH₂-N(CH₂CH₃)(CH₂CH₃) |
| 150 | H | X₂—CH₂—CH₃ (wedge) | R | X₃-CH₂-CH₂-CH(CH₃)-CH₃ | H | X₅-CH₂-CH₂-piperidin-1-yl |

TABLE 1-continued

| Example No. | R¹ | R² | config. R¹ or R² | R³ | R⁴ | Lₙ—R⁵ₘ |
|---|---|---|---|---|---|---|
| 151 | H | X₂—CH₃ | R | X₃—CH₂CH(CH₃)₂ (isobutyl via CH₂) H₃C-CH-CH₃ | CH₃—O—X₄ | X₅—(CH₂)₃—morpholine |
| 152 | H | X₂—CH₃ | R | X₃—CH₂CH(CH₃)CH₃ | CH₃—O—X₄ | X₅—(CH₂)₃—N-methylpiperazine |
| 153 | H | X₂—CH₃ | R | X₃—CH₂CH(CH₃)CH₃ | CH₃—O—X₄ | X₅—(CH₂)₄—N(CH₂CH₃)₂ |
| 154 | H | X₂—CH₃ | R | X₃—CH₂CH(CH₃)CH₃ | H | X₅—(CH₂)₃—N-methylpiperazine |
| 155 | H | X₂—CH₃ | R | X₃—CH₂CH(CH₃)CH₃ | H | X₅—(CH₂)₃—morpholine |

TABLE 1-continued

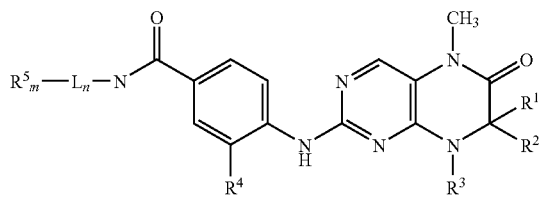

| Example No. | R¹ | R² | config. R¹ or R² | R³ | R⁴ | Lₙ—R⁵ₘ |
|---|---|---|---|---|---|---|
| 156 | H | X₂—CH₂—CH₃ | R | X₃—CH₂—CH₂—CH(CH₃)—CH₃ | CH₃—O—X₄ | X₅—CH₂—CH₂—N(morpholine) |
| 157 | H | X₂—CH₂—CH₃ | R | X₃—CH₂—CH₂—CH(CH₃)—CH₃ | CH₃—O—X₄ | X₅—CH₂—CH₂—CH₂—N(pyrrolidine) |
| 158 | H | X₂—CH₂—CH₃ | R | X₃—CH₂—CH₂—CH(CH₃)—CH₃ | CH₃—O—X₄ | X₅—CH₂—CH₂—N(CH₂CH₃)₂ |
| 159 | H | X₂—CH₂—CH₃ | R | X₃—CH₂—CH₂—CH(CH₃)—CH₃ | CH₃—O—X₄ | X₅—CH₂—CH₂—N(CH₃)₂ |
| 160 | H | X₂—CH₂—CH₃ | R | X₃—CH₂—CH₂—CH(CH₃)—CH₃ | CH₃—O—X₄ | X₅—CH₂—CH₂—N(CH(CH₃)₂)₂ |
| 161 | X₁—CH₃ | X₂—CH₃ | | X₃—CH₂—CH₂—CH(CH₃)—CH₃ | H₃C—O—X₄ | X₅—CH₂—CH₂—N(CH₂CH₃)₂ |

TABLE 1-continued

| Example No. | R¹ | R² | config. R¹ or R² | R³ | R⁴ | L$_n$—R⁵$_m$ |
|---|---|---|---|---|---|---|
| 162 | X₁—CH₃ | X₂—CH₃ | | X₃—CH₂CH(CH₃)₂ (isobutyl on X₃) | H₃C—O—X₄ | X₅-(1-methylpiperidin-4-yl) |
| 163 | H | X₂—CH₂CH₃ | R | X₃—CH₂CH(CH₃)₂ | H₃C—O—X₄ | X₅-(quinuclidin-3-yl) |
| 164 | H | X₂—CH₂CH₃ | R | X₃—CH₂CH(CH₃)₂ | H₃C—O—X₄ | X₅—(CH₂)₃—N(CH₃)₂ |
| 165 | H | X₂—CH₂CH₃ | R | X₃—CH₂CH(CH₃)₂ | H₃C—O—X₄ | X₅—(CH₂)₃—N(CH₂CH₃)₂ |
| 166 | H | X₁—CH₂CH₃ | R | X₃-cyclopentyl | H₃C—O—X₄ | X₅-(4-(morpholinomethyl)phenyl) |
| 167 | H | X₂—CH₂CH₃ | R | X₃—CH₂CH(CH₃)₂ | H₃C—O—X₄ | X₅—CH₂CH₂-(1-methylpyrrolidin-2-yl) |

TABLE 1-continued

| Example No. | R¹ | R² | config. R¹ or R² | R³ | R⁴ | $L_n$—$R^5_m$ |
|---|---|---|---|---|---|---|
| 168 | H | $X_2$—CH₂CH₃ | R | $X_3$—CH₂CH(CH₃)₂ | CH₃O—$X_4$ | $X_5$—CH₂C(CH₃)₂CH₂N(CH₃)₂ |
| 169 | H | $X_2$—CH₂CH₃ | R | $X_3$—CH₂CH(CH₃)₂ | CH₃O—$X_4$ | $X_5$—(CH₂)₃-piperidinyl |
| 170 | H | $X_2$—CH₂CH₃ | R | $X_3$—CH₂CH(CH₃)₂ | CH₃O—$X_4$ | $X_5$—(CH₂)₂-pyrrolidinyl |
| 171 | H | $X_2$—CH₂CH₃ | R | $X_3$—CH₂CH(CH₃)₂ | CH₃O—$X_4$ | $X_5$-(N-methylpiperidin-4-yl) |
| 172 | H | $X_2$—CH₂CH₃ | R | $X_3$—CH₂CH(CH₃)₂ | CH₃O—$X_4$ | $X_5$-(N-methylazepan-4-yl) |
| 173 | H | $X_2$—CH₂CH₃ | R | $X_3$—CH₂CH(CH₃)₂ | CH₃O—$X_4$ | $X_5$-(N-methyltropanyl) |

TABLE 1-continued

| Example No. | R¹ | R² | config. R¹ or R² | R³ | R⁴ | Lₙ—R⁵ₘ |
|---|---|---|---|---|---|---|
| 174 | H | X₂–CH₂–CH₃ | R | X₃–CH₂–CH(CH₃)₂ | CH₃–O–X₄ | 1-benzylpiperidin-4-yl (X₅) |
| 175 | H | X₂–CH₃ | R | cyclopentyl (X₃) | CH₃–O–X₄ | X₅–C(CH₃)₂–CH₂–N(CH₃)₂ |
| 176 | H | X₂–CH₂–CH₃ | R | X₃–CH(CH₃)₂ | CH₃–O–X₄ | X₅–C(CH₃)₂–CH₂–N(CH₃)₂ |
| 177 | H | X₂–CH₂–CH₃ | R | cyclopentyl (X₃) | CH₃–O–X₄ | X₅–C(CH₃)₂–CH₂–N(CH₃)₂ |
| 178 | H | X₂–CH₃ | R | X₃–CH(CH₃)₂ | CH₃–O–X₄ | piperidin-4-yl (X₅) |
| 179 | H | X₂–CH₂–CH₃ | R | X₃–CH₂–CH(CH₃)₂ | CH₃–O–X₄ | piperidin-4-yl (X₅) |

TABLE 1-continued

| Example No. | R¹ | R² | config. R¹ or R² | R³ | R⁴ | Lₙ—R⁵ₘ |
|---|---|---|---|---|---|---|
| 180 | H | X₂—CH₃ (ethyl) | R | cyclohexyl-X₃ | H₃C—O—X₄ | X₅-(1-benzylpiperidin-4-yl) |
| 181 | H | X₂—CH₃ | R | tetrahydropyran-4-yl-X₃ | CH₃—O—X₄ | X₅-(1-benzylpiperidin-4-yl) |
| 182 | H | X₂—CH₃ | R | cyclopentyl-X₃ | CH₃—O—X₄ | H₃C–C(CH₃)(X₅)–CH₂–morpholine |
| 183 | H | X₂—CH₃ (ethyl) | R | isopropyl-X₃ (CH(CH₃)₂) | CH₃—O—X₄ | H₃C–C(CH₃)(X₅)–CH₂–morpholine |
| 184 | H | X₂—CH₃ (ethyl) | R | cyclopentyl-X₃ | CH₃—O—X₄ | H₃C–C(CH₃)(X₅)–CH₂–morpholine |

TABLE 1-continued

| Example No. | R¹ | R² | config. R¹ or R² | R³ | R⁴ | Lₙ—R⁵ₘ |
|---|---|---|---|---|---|---|
| 185 | H | X₂—CH₃ | R | X₃–(4-methoxyphenyl) | CH₃O—X₄ | H₃C–C(CH₃)₂–CH₂–morpholine–X₅ |
| 186 | H | X₂—CH₃ | R | X₃–cyclohexyl | CH₃O—X₄ | X₅–(4-(4-methylpiperazin-1-yl)phenyl) |
| 187 | H | X₂—CH₂—CH₃ | R | X₃–cyclopentyl | CH₃O—X₄ | X₅–(4-(4-methylpiperazin-1-yl)phenyl) |
| 188 | H | X₂—CH₃ | R | X₃–cyclopentyl | Cl—X₄ | X₅–(1-methylpiperidin-4-yl) |

TABLE 1-continued

| Example No. | R¹ | R² | config. R¹ or R² | R³ | R⁴ | Lₙ—R⁵ₘ |
|---|---|---|---|---|---|---|
| 189 | H | X₂–CH₂CH₃ | R | X₃–cyclohexyl | X₄–O–CH₃ | X₅–(trans-cyclohexyl)–N-morpholine |
| 190 | H | X₂–CH₃ | R | X₃–cyclopentyl | CH₃–O–X₄ | X₅–piperidin-4-yl |
| 191 | H | X₂–cyclopropyl | R | X₃–CH(CH₃)₂ | H₃C–CH₂–O–X₄ | X₅–(1-methylpiperidin-4-yl) |
| 192 | H | X₂–CH₃ | R | X₃–cyclohexyl | CH₃–O–X₄ | H₃C–C(CH₃)₂–CH₂–N-morpholine, X₅ |
| 193 | H | X₂–CH₂CH₃ | R | X₃–cyclohexyl | CH₃–O–X₄ | H₃C–C(CH₃)₂–CH₂–N-morpholine, X₅ |
| 194 | H | X₂–CH₂CH₃ | R | X₃–phenyl | CH₃–O–X₄ | H₃C–C(CH₃)₂–CH₂–N-morpholine, X₅ |

TABLE 1-continued

| Example No. | R¹ | R² | config. R¹ or R² | R³ | R⁴ | Lₙ—R⁵ₘ |
|---|---|---|---|---|---|---|
| 195 | H | X₂—CH₃ (wedge) | R | X₃–CH₂–CH(CH₃)₂ | CH₃–O–X₄ | H₃C–C(CH₃)₂–CH₂–N(morpholine), X₅ |
| 196 | H | X₂–CH₂CH₃ | R | X₃–CH₂–CH₂–CH(CH₃)₂ | CH₃–O–X₄ | H₃C–C(CH₃)₂–CH₂–N(4-methylpiperazine), X₅ |
| 197 | H | X₂–cyclopropyl | R | X₃–CH₂–CH₂–CH(CH₃)₂ | CH₃–O–X₄ | H₃C–C(CH₃)₂–CH₂–N(4-methylpiperazine), X₅ |
| 198 | H | X₃,X₂–cyclobutyl (spiro) | R | | H₃C–O–X₄ | X₅–(1-methylpiperidin-4-yl) |
| 199 | H | X₃,X₂–cyclobutyl (spiro) | R | | H₃C–O–X₄ | X₅–(trans-4-morpholinocyclohexyl) |

TABLE 1-continued

| Example No. | R¹ | R² | config. R¹ or R² | R³ | R⁴ | $L_n$—$R^5{}_m$ |
|---|---|---|---|---|---|---|
| 200 | H | X₂–(cyclohexyl with X₃) | R | | CH₃O–X₄ | X₅–(1-methylpiperidin-4-yl) |
| 201 | H | X₂–(cyclohexyl with X₃) | R | | CH₃O–X₄ | X₅–(1-benzylpiperidin-4-yl) |
| 202 | X₁–CH₃ | X₂–CH₃ | | X₃–CH₂CH(CH₃)₂ (isobutyl) | CH₃O–X₄ | X₅–(4-(morpholinomethyl)phenyl) |
| 203 | H | X₂–CH₃ (wedge) | R | X₃–cyclopentyl | Cl–X₄ | X₅–(1-benzylpiperidin-4-yl) |
| 204 | H | X₂–CH₃ (wedge) | R | X₃–CH₂CH(CH₃)₂ (isobutyl) | CH₃O–X₄ | X₅–(1-benzylpiperidin-4-yl) |

TABLE 1-continued
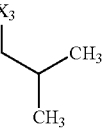
| Example No. | R¹ | R² | config. R¹ or R² | R³ | R⁴ | Lₙ—R⁵ₘ |
|---|---|---|---|---|---|---|
| 205 | H | X₂—CH₃ | R | X₃—CH₂CH(CH₃)CH₃ | X₄—O—CH₃ |  |
| 206 | H | X₂—CH₃ | R | X₃—CH₂C(CH₃)₃ | X₄—O—CH₃ | 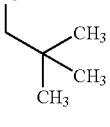 |
| 207 | H | X₂—CH₃ | R | X₃—CH₂C(CH₃)₃ | X₄—O—CH₃ | 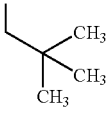 |
| 208 | H | X₂—CH₃ | R | X₃—CH₂C(CH₃)₃ | X₄—O—CH₃ | 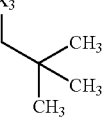 |

TABLE 1-continued
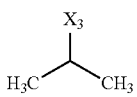
| Example No. | R¹ | R² | config. R¹ or R² | R³ | R⁴ | Lₙ—R⁵ₘ |
|---|---|---|---|---|---|---|
| 209 | H | X₂—CH₃ | R |  | X₄—O—CH₃ | 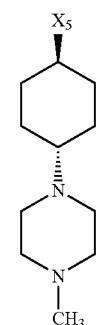 |
| 210 | H | X₂—CH₃ | R | 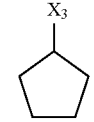 | X₄—O—CH₃ | 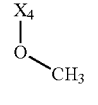 |
| 211 | X₁—CH₃ | X₂—CH₃ | | 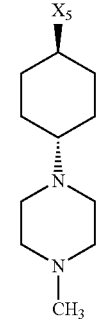 | X₄—O—CH₃ | 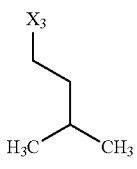 |
| 212 | X₁—CH₃ | X₂—CH₃ | |  | X₄—O—CH₃ | 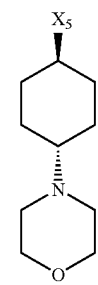 |

TABLE 1-continued

| Example No. | R¹ | R² | config. R¹ or R² | R³ | R⁴ | $L_n$—$R^5_m$ |
|---|---|---|---|---|---|---|
| 213 | H | X₂—CH₃ | R | X₃-cyclohexyl | X₄—O—CH₃ | X₅-cyclohexyl-piperazine-C(O)CH₃ |
| 214 | H | X₂—CH₃ | R | X₃-CH(CH₃)₂ | X₄—O—CH₃ | X₅-cyclohexyl-piperazine-N-CH₃ |
| 215 | X₁—CH₃ | X₂—CH₃ | | X₃—CH₂CH(CH₃)₂ | X₄—O—CH₃ | X₅-cyclohexyl-piperazine-N-CH₃ |
| 216 | H | X₂—CH₃ | R | X₃-cyclohexyl | X₄—O—CH₃ | X₅-cyclohexyl-piperazine-N-CH₃ |

TABLE 1-continued
| Example No. | R¹ | R² | config. R¹ or R² | R³ | R⁴ | Lₙ—R⁵ₘ |
|---|---|---|---|---|---|---|
| 217 | H | X₂⁓CH₃ | R |  cyclopentyl with X₃ | X₄—O—CH₃ | 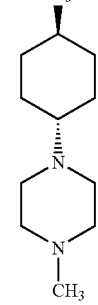 |
| 218 | H | X₂⁓CH₃ | R | 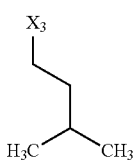 | X₄—O—CH₃ |  |
| 219 | H | X₂⁓CH₃ | R | 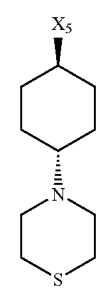 | X₄—O—CH₃ | 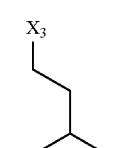 |
| 220 | H | X₂⁓CH₃ | R |  | X₄—O—CH₃ | 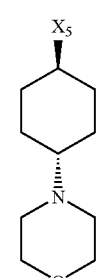 |

TABLE 1-continued

| Example No. | R¹ | R² | config. R¹ or R² | R³ | R⁴ | Lₙ—R⁵ₘ |
|---|---|---|---|---|---|---|
| 221 | H | X₂–CH₃ | R | X₃–CH₂CH₂–CH(CH₃)₂ | X₄–O–CH₃ | X₅–(trans-cyclohexyl)–N(piperazine)–N–CH₃ |
| 222 | H | X₂–CH₂CH₃ | R | X₃–CH₂CH₂–CH(CH₃)₂ | X₄–O–CH₃ | X₅–(trans-cyclohexyl)–N(piperazine)–N–CH₃ |
| 223 | H | X₂–CH₃ | R | X₃–phenyl | X₄–O–CH₂CH₃ | X₅–(piperidine)–N–CH₃ |
| 224 | H | X₂–CH₃ | R | X₃–(3-methoxyphenyl) | X₄–O–CH₃ | X₅–(piperidine)–N–CH₃ |
| 225 | H | X₂–CH₃ | R | X₃–(3-methoxyphenyl) | H | X₅–(piperidine)–N–CH₃ |

TABLE 1-continued

| Example No. | R¹ | R² | config. R¹ or R² | R³ | R⁴ | Lₙ—R⁵ₘ |
|---|---|---|---|---|---|---|
| 226 | H | X₂⬩CH₃ | R | X₃-(2-methoxyphenyl) | H₃C-O-X₄ | X₅-(1-methylpiperidin-4-yl) |
| 227 | H | X₂⬩CH₃ | R | X₃-(2-methoxyphenyl) | CH₃-O-X₄ | H₃C-C(CH₃)-CH₂-N(pyrrolidine)-X₅ |
| 228 | H | X₂⬩CH₃ | R | X₃-CH₂CH₂CH(CH₃)₂ | X₄-O-CH₃ | X₅-(trans-4-(4,4-dimethylpiperidin-1-yl)cyclohexyl) |
| 229 | H | X₂-CH₂CH₃ | R | X₃-phenyl | CH₃-O-X₄ | H₃C-C(CH₃)-CH₂-N(piperidine)-X₅ |
| 230 | H | X₂⬩CH₃ | R | X₃-cyclohexyl | CH₃-O-X₄ | H₃C-C(CH₃)-CH₂-N(piperidine)-X₅ |

TABLE 1-continued

| Example No. | R¹ | R² | config. R¹ or R² | R³ | R⁴ | $L_n$—$R^5_m$ |
|---|---|---|---|---|---|---|
| 231 | H | X₂–CH₃ (wedge) | R | X₃-cyclopentyl | X₄–O–CH₃ | X₅–CH₂–C(CH₃)₂–CH₂–N(piperidine) |
| 232 | H | X₂–CH₃ (wedge) | R | X₃-cyclohexyl | X₄–O–CH₃ | X₅-trans-cyclohexyl-piperazine |
| 233 | H | X₁–CH₃ (wedge) | R | X₃–CH₂–C(CH₃)₃ | X₄–O–CH₃ | X₅-trans-cyclohexyl-(2,6-cis-dimethylmorpholine) |
| 234 | H | X₁–CH₃ | R | X₃–CH(CH₃)₂ | X₄–O–CH₃ | X₅-trans-cyclohexyl-(2,6-cis-dimethylmorpholine) |

TABLE 1-continued

| Example No. | R¹ | R² | config. R¹ or R² | R³ | R⁴ | L_n—R⁵_m |
|---|---|---|---|---|---|---|
| 235 | H | X₁—CH₃ | R | X₃—CH₂CH₂CH(CH₃)₂ | X₄—O—CH₃ | X₅-cyclohexyl-N-thiomorpholine S-oxide |
| 236 | H | X₁—CH₃ | R | X₃—CH₂CH₂CH(CH₃)₂ | X₄—O—CH₃ | X₅-cyclohexyl-N-thiomorpholine S-oxide |
| 237 | H | X₁—CH₂CH₃ | R | X₃—CH(CH₃)₂ | CH₃—O—X₄ | X₅-piperidine |
| 238 | H | X₁—CH₃ | R | X₃-cyclopentyl | CH₃—O—X₄ | X₅-piperidine |

TABLE 1-continued

| Example No. | R¹ | R² | config. R¹ or R² | R³ | R⁴ | Lₙ—R⁵ₘ |
|---|---|---|---|---|---|---|
| 239 | H | X₁—CH₃ (wedge) | R | X₃-cyclopentyl | CH₃-O-X₄ | H₃C-C(X₅)(CH₃)-CH₂-N(morpholine) |
| 240 | H | X₁—CH₃ | R | X₃-cyclohexyl | CH₃-O-X₄ | H₃C-C(X₅)(CH₃)-CH₂-N(CH₃)₂ |
| 241 | H | X₁—CH₃ | R | X₃-CH₂CH₂CH(CH₃)₂ (isopentyl) | CH₃-O-X₄ | H₃C-C(X₅)(CH₃)-CH₂-N(4-methylpiperazine) |
| 242 | H | X₁—CH₃ | R | X₃-CH₂CH₂CH(CH₃)₂ | CH₃-O-X₄ | X₅-CH₂CH₂-N(piperidine) |
| 243 | H | X₁—CH₃ | R | X₃-CH₂CH₂CH(CH₃)₂ | CH₃-O-X₄ | X₅-CH₂CH₂CH₂-N(CH₃)₂ |
| 244 | H | X₁—CH₃ | R | X₃-CH₂CH₂CH(CH₃)₂ | CH₃-O-X₄ | X₅-CH₂CH₂CH₂-N(4-methylpiperazine) |

105
The following examples of synthesis are to be construed as examples of the procedure for further illustration of the invention without restricting it to their content. The syntheses are illustrated in Diagrams (1) to (3).
106
Synthesis of Compound of Example No. 46
Synthesis Diagram 1
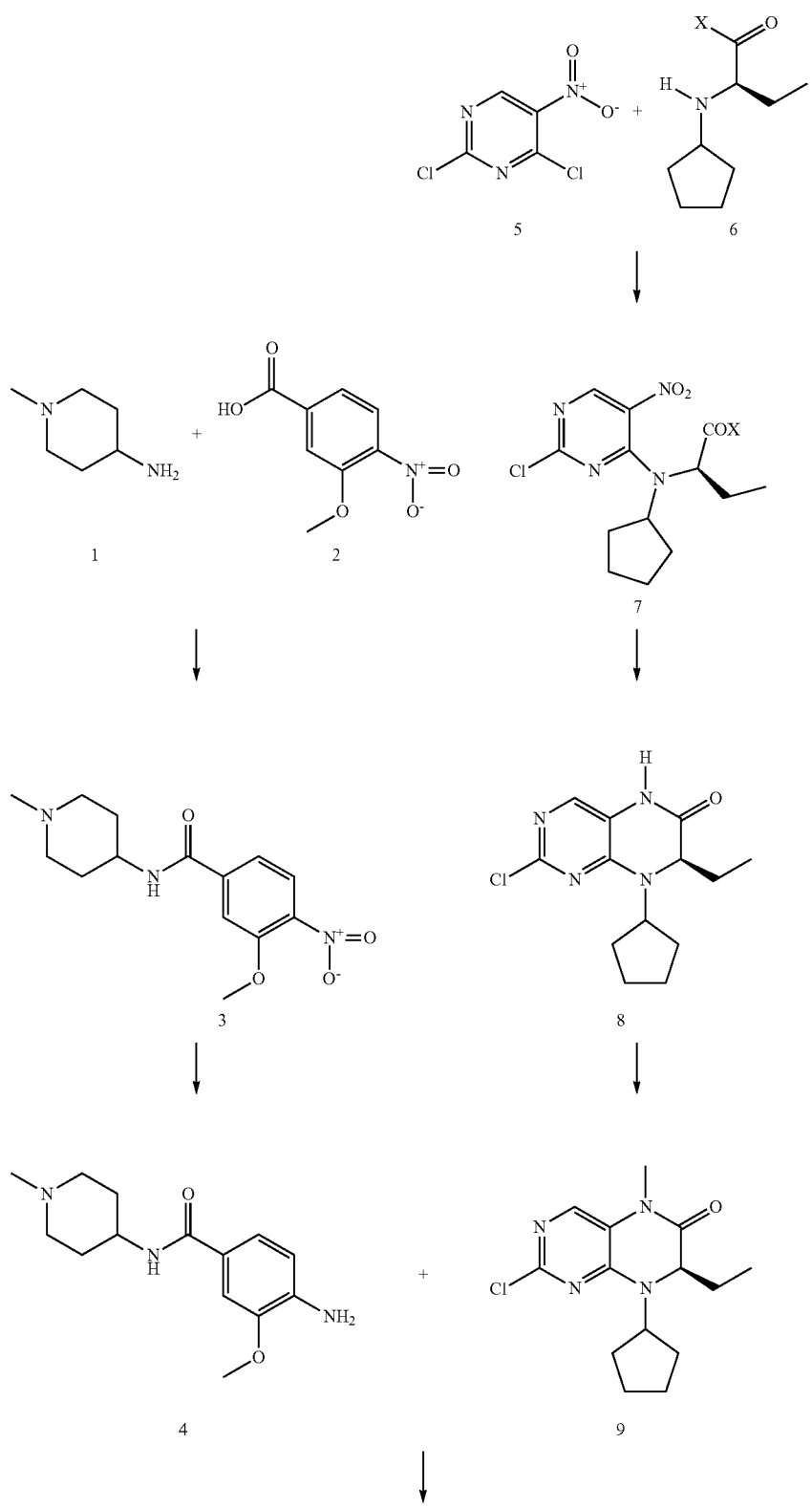

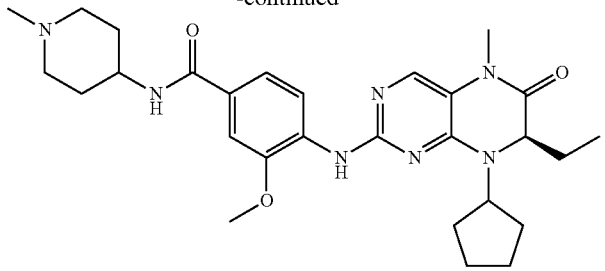

Example 46

Preparation of the Aniline Fragment 4 by:
Preparation of the Compound 3

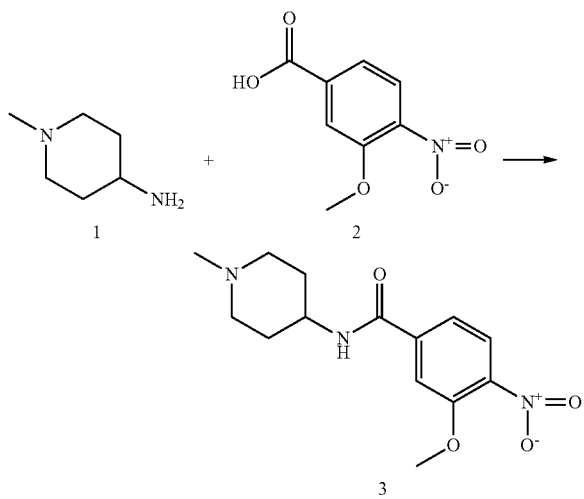

Variant 1A:

A suspension of 100 g (0.507 mol) 3-methoxy-4-nitrobenzoic acid 2, 163 g (0.508 mol) O-(benzotriazol-1-yl)-N,N,N',N'-tetramethyluronium tetrafluoroborate and 192 mL (1.1 mol) ethyldiisopropylamine in 1.2 L dichloromethane is stirred for one hour at 25° C. 58 g (0.508 mol) 1-methyl-4-aminopiperidine 1 are added to the solution formed and it is stirred for 16 hours at 20° C. The solution is evaporated down to 600 mL and the organic phase is washed five times with 80 mL 1 molar ammonia solution. The organic phase is concentrated by evaporation and the residue is chromatographed with dichloromethane/methanol/conc. ammonia (15:1:0.1) through silica gel. Product fractions are combined, the solvent is evaporated off and the product is crystallised from ethyl acetate/methanol. 123 g product 3 are obtained.

Variant 1B:

4.00 kg (20.3 mol) 3-methoxy-4-nitrobenzoic acid 2 are placed in 54 L toluene. At normal pressure 16 L toluene are distilled off. The mixture is cooled to 105° C. and 40 ml of dimethylformamide in 2 L toluene are added. At a jacket temperature of 120° C., 2.90 kg (24.3 mol) thionyl chloride are allowed to flow in within 30 min. and the mixture is rinsed with 4 L toluene. The reaction mixture is stirred for 1 hour at reflux temperature. Then 12 L toluene are distilled off under normal pressure. The contents of the reactor are cooled. A solution of 2.55 kg (22.3 mol) 1-methyl-4-aminopiperidine 1 in 2 L toluene and 2.46 kg (24.3 mol) triethylamine in 2 L toluene is allowed to flow in at 55-65° C. The mixture is rinsed with 4 L toluene. The suspension is stirred for 1 hour. 20 L water are allowed to flow in and at 35-40° C. 3.08 kg (30.4 mol) conc. hydrochloric acid (36%) are added. The mixture is rinsed with 2 L water. At 35-40° C. 2 phases are formed. The organic phase is separated off and the aqueous phase containing the product is returned to the reactor. It is rinsed with 4 L water. Under reduced pressure 3.2 L water are distilled off at 50° C. 4.87 kg (60.9 mol) sodium hydroxide solution (50%) is allowed to flow into the remaining solution at 40° C. It is rinsed with 4 L water. The product suspension is allowed to cool to 22° C. and stirred for 30 min. at this temperature. The suspension is suction filtered and the filter cake is washed with 40 L water. The product is dried at 40° C. in the vacuum drying cupboard. 5.65 kg product are obtained.

Preparation of the Compound 4:

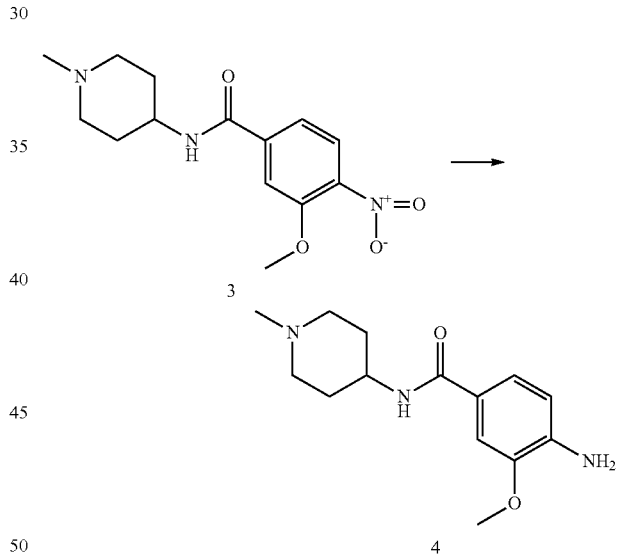

Variant 2A

A solution of 145 g (0.494 mol) 3 in 2 L methanol is hydrogenated at 4 bar in the presence of 2 g palladium on charcoal (10%). The catalyst is filtered off and the filtrate is concentrated by evaporation. 128 g product 4 are obtained.

Variant 2B

25 L demineralised water are added to 5.00 kg (17.0 mol) 3 and 600 g activated charcoal (industrial-grade). Then 2.05 kg (34.1 mol) acetic acid are added. The suspension is stirred for 15 minutes at 22-25° C. 500 g palladium on charcoal (10%) suspended in 3 L demineralised water are added and the mixture is rinsed with 2 L demineralised water. The contents of the reactor are heated to 40° C. and hydrogenated at this temperature until the hydrogen uptake stops. The reaction mixture is filtered and the filter cake is washed with 10 L demineralised water.

For crystallisation the filtrate is transferred into a reactor and the transporting vessel is rinsed with 5 L demineralised water. The contents of the reactor are heated to 50° C. A mixture of 5.45 kg (68.2 mol) sodium hydroxide solution (50%, industrial-grade) and 7 L demineralised water is added. The mixture is stirred for 10 minutes at 45-50° C. The suspension is cooled to 20° C. and stirred for 1-1.5 hours at this temperature. The product is suction filtered, washed with 30 L demineralised water and dried at 45° C. in the vacuum drying cupboard. 4.13 kg product 4 are obtained.

Preparation of the Dihydropteridinone Fragment 9, by:
Preparation of the Amino Acid Ester 6a-d

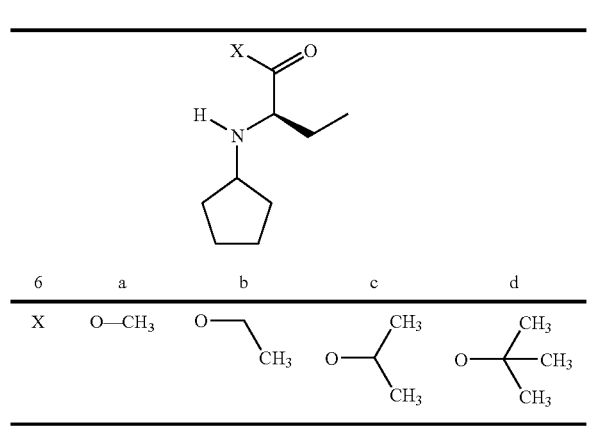

| 6 | a | b | c | d |
|---|---|---|---|---|
| X | O—CH₃ | O—CH₂—CH₃ | O—CH(CH₃)₂ | O—C(CH₃)₃ |

The methyl ester 6a, ethyl ester 6b and 2-propyl ester 6c are prepared by methods known from the literature, for example according to WO 03/020722 A1. The tert.-butyl ester 6d is prepared by transesterification with tert. butyl acetate in the presence of perchloric acid (J. Med. Chem., Vol 37, No 20, 1994, 3294-3302).

The amino acids may be used in the form of the bases or as hydrochlorides in the following nucleophilic substitution reaction.

Preparation of the Amino Acid Amides 6e,f

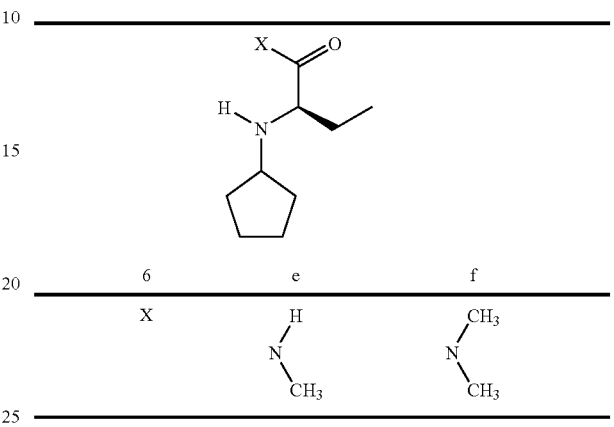

| 6 | e | f |
|---|---|---|
| X | N(H)CH₃ | N(CH₃)₂ |

The amino acid amide 6e is prepared by aminolysis of the methyl ester 6a with 40% aqueous methylamine solution at ambient temperature.

The amino acid amide 6f is prepared by amide formation of the free amino acid with a fivefold excess of 2 molar dimethylamine solution in tetrahydrofuran in the presence of O-(benzotriazol-1-yl)-N,N,N',N'-tetramethyluronium tetrafluoroborate as coupling reagent.

Preparation of the Compounds 7

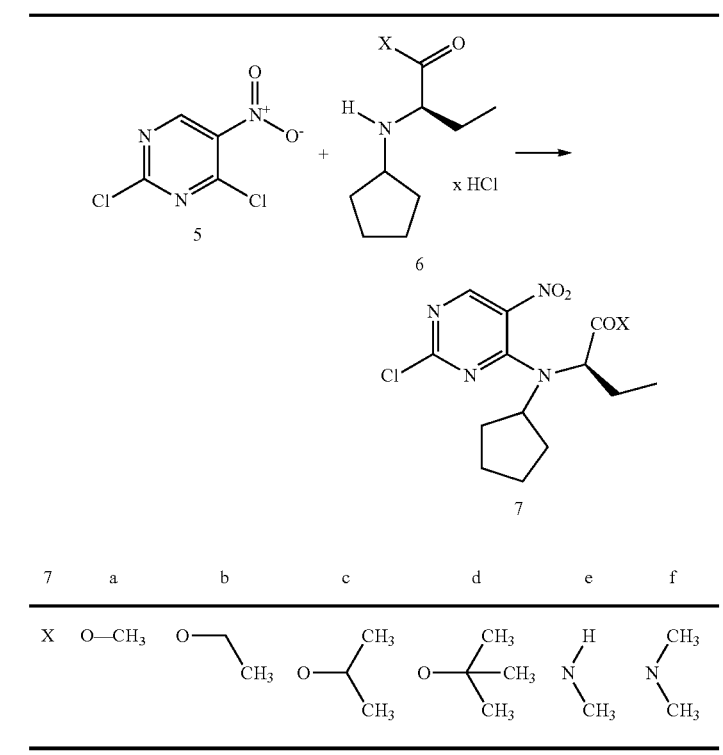

| 7 | a | b | c | d | e | f |
|---|---|---|---|---|---|---|
| X | O—CH₃ | O—CH₂—CH₃ | O—CH(CH₃)₂ | O—C(CH₃)₃ | N(H)CH₃ | N(CH₃)₂ |

Preparation of the methyl ester 7a

A suspension of 457 g (2.06 mol) of the amino acid methyl ester 6a and 693 g (8.25 mol) powdered sodium hydrogen carbonate in 10 L cyclohexane is stirred for 15 minutes at ambient temperature. 440 g (2.27 mol) 2,4-dichloro-5-nitro-pyrimidine 5 and 1.5 L cyclohexane are added and the mixture is stirred for 3 days at ambient temperature. The reaction is monitored by HPLC. In order to redissolve any product which has crystallised out, 4 L of dichloromethane are added to the suspension. After the addition of 335 g magnesium sulphate the suspension is suction filtered and the inorganic filter cake is washed again with dichloromethane. The filtrate is evaporated down to 3.1 kg under reduced pressure and the suspension obtained is refluxed. The solution is allowed to cool slowly and stirred for one hour at 10-15° C. The suspension is suction filtered and the filter cake is washed with cyclohexane. The product is dried at 40° C. in the vacuum drying cupboard. 582 g of 7a (X=OCH₃) are obtained as a dark yellow solid.

Compounds 7b-f are prepared analogously to this method. During the reaction of the amino acid amide 7e,f a fairly polar solvent such as e.g. ethyl acetate or dichloromethane is added to improve solubility.

Preparation of Compound 8

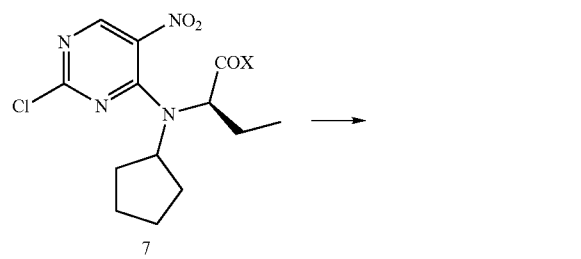

7

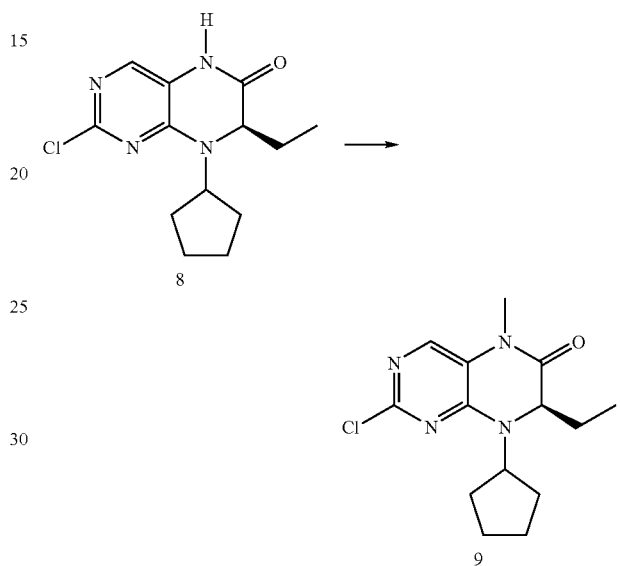

8

A freshly prepared suspension of 560 g (1.63 mol) 7a and 185 g Raney nickel in 2.8 L acetic acid is hydrogenated at 75° C. After the uptake of hydrogen has ended the catalyst is filtered off and the hydrogenation solution is evaporated down under reduced pressure. 4 L of demineralised water and 4 L ethyl acetate are added to the residue. A precipitate which contains the product is formed between the phases. The aqueous phase is separated off. 2 L ethyl acetate are added to the organic phase and the precipitate is suction filtered. The precipitate is suspended in 600 mL demineralised water, stirred for 1 hour at ambient temperature, suction filtered and washed with demineralised water. 110 g of moist product A are obtained.

The filtrate is washed three times with sodium chloride solution. The organic phase is concentrated by evaporation. 380 g of a reddish-brown residue B are obtained, which is combined with the moist product A. The combined crude products A and B are dissolved in 1.5 L ethanol at reflux temperature. The solution is filtered clear and the filter is rinsed with 150 mL ethanol. 550 mL demineralised water are added to the solution at reflux temperature. The mixture is left to cool and stirred for 16 hours at ambient temperature and for 3 hours at 0-5° C. The precipitate is suction filtered and washed with demineralised water/methanol (1:1) and then with demineralised water. The product is dried at 50° C. in the vacuum drying cupboard. 266 g product 8 are obtained as a solid.

Preparation of Compound 9

38 g (0.95 mol) sodium hydride (60% dispersion in mineral oil) are added batchwise to a solution of 264 g (0.94 mol) of 8 and 161 g (1.13 mol) methyl iodide in 2 L dimethylacetamide at 4-10° C. within one hour. The cooling bath is removed and the mixture is allowed to come up to 20° C. within 2 hours. It is cooled to 10° C. and a further 0.38 g (9.5 mmol) sodium hydride are added. The mixture is stirred for 4 hours at 10-15° C. 100 mL ethyl acetate and 1 kg ice are added to the reaction solution. The resulting suspension is diluted with 3 L demineralised water. The suspension is stirred for 2 hours, the precipitate is suction filtered and the filter cake is washed with demineralised water. The product is dried at 50° C. in the vacuum drying cupboard. 273 g of product 9 are obtained as colourless crystals.

Preparation of the Compound of Example No. 46 by Reacting 4 with 9

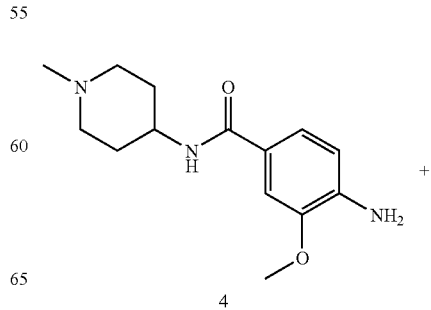

4

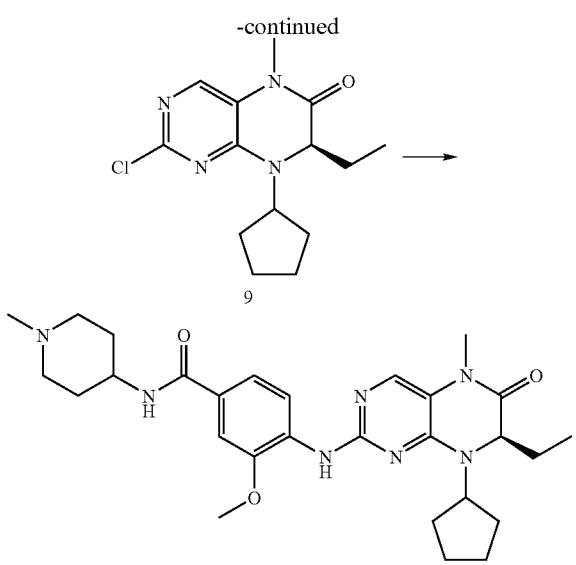

9

A suspension of 201 g (1.06 mol) para-toluenesulphonic acid-hydrate, 209 g (706 mmol) 9 and 183 g (695 mmol) 4 in 800 mL 2-methyl-4-pentanol is refluxed. 100 mL solvent are distilled off. The mixture is refluxed for 3 hours, 200 mL of 2-methyl-4-pentanol are added and 120 mL of solvent are distilled off. After 2 hours heating at reflux temperature a further 280 mL solvent are distilled off. The mixture is cooled to 100° C. and 1 L demineralised water and then 0.5 L ethyl acetate are added to the reaction solution. The organic phase is separated off and the aqueous phase is again washed with 0.5 L ethyl acetate. 1.5 L dichloromethane and 0.5 L ethyl acetate are added to the acidic aqueous phase. The pH value of the aqueous phase is adjusted to pH 9.2 with 260 mL of 6 normal sodium hydroxide solution. The aqueous phase is separated off and the organic phase is washed three times with in each case 1 L of 1 normal aqueous sodium hydrogen carbonate solution. The organic phase is dried over sodium sulphate, filtered and the solvent is evaporated down under reduced pressure. 406 g of crude product are obtained.

The crude product is dissolved in 1.5 L ethyl acetate. At a temperature of 50-55° C. 2.5 L of methyl-tert.-butylether are added. The mixture is inoculated at 45° C. and stirred for 16 hours with cooling to ambient temperature. The suspension is stirred for 3.5 hours at 0-5° C. and the precipitate is suction filtered. The filter cake is washed again with methyl-tert.-butylether/ethyl acetate (2:1) and methyl-tert.-butylether. The product is dried at 50° C. in the vacuum drying cupboard. 236 g of crystalline compound of Example no. 46 are obtained as the anhydrate (I).

Crystallisation:

46.5 g of the crystalline anhydrate (I) described above are dissolved in 310 mL of 1-propanol and filtered clear. The mixture is heated to 70° C. and 620 mL demineralised water are added. The solution is left to cool to ambient temperature, cooled to 0-10° C. and seed crystals are added. The resulting suspension is stirred for 3 hours at 0-10° C. It is suction filtered and washed with cold 1-propanol/demineralised water (1:2) and demineralised water. The product is dried at 50° C. in the vacuum drying cupboard. 40.5 g crystalline compound of Example No. 46 are obtained as the monohydrate.

The crude product of the reaction described above may also be crystallised directly as the crystalline monohydrate from 1-propanol/demineralised water.

Synthesis of the Compounds of Example No. 27, Example No. 110 and Example No. 234

Synthesis Diagram 2

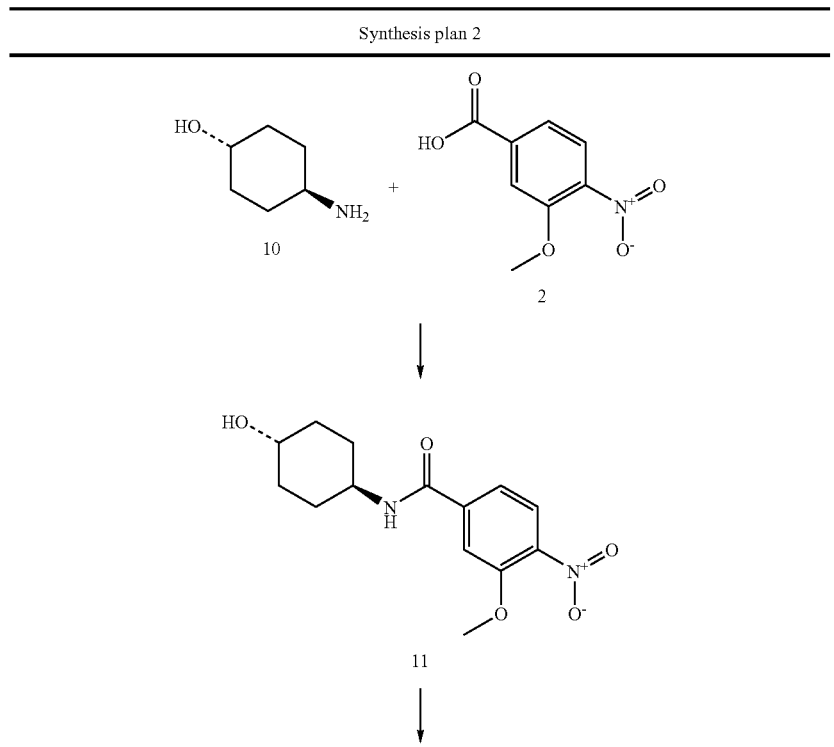

-continued
Synthesis plan 2
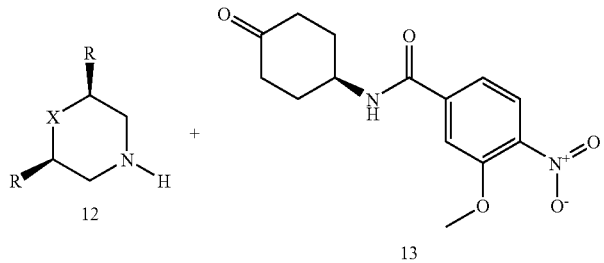
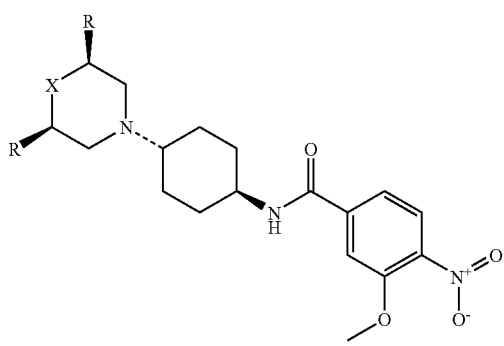
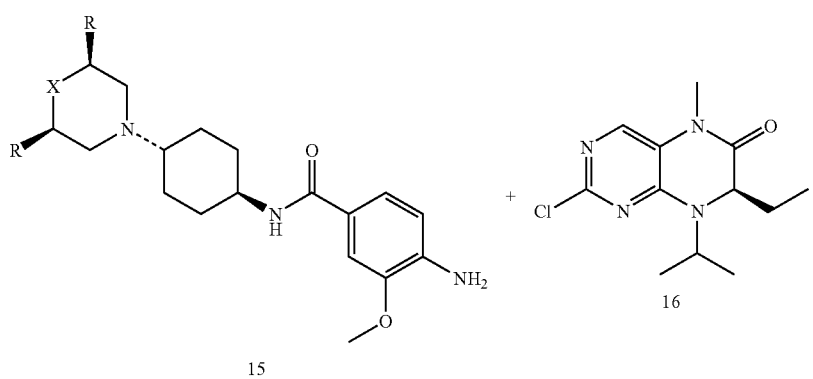

-continued

Synthesis plan 2

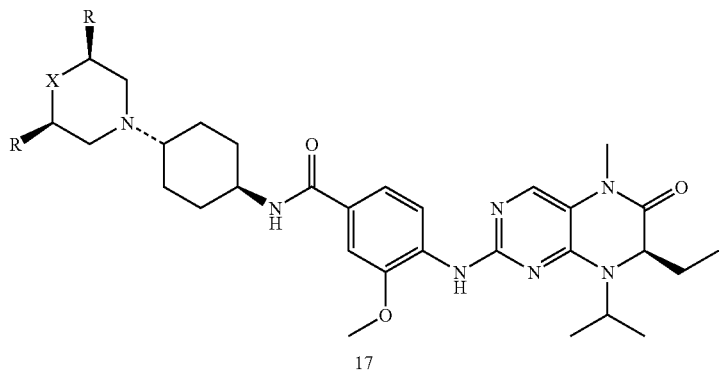

| 17 | R   | X           |
|----|-----|-------------|
| a  | CH3 | O           |
| b  | H   | O           |
| c  | H   | N—CH2-cyclopropyl |

Preparation of 11

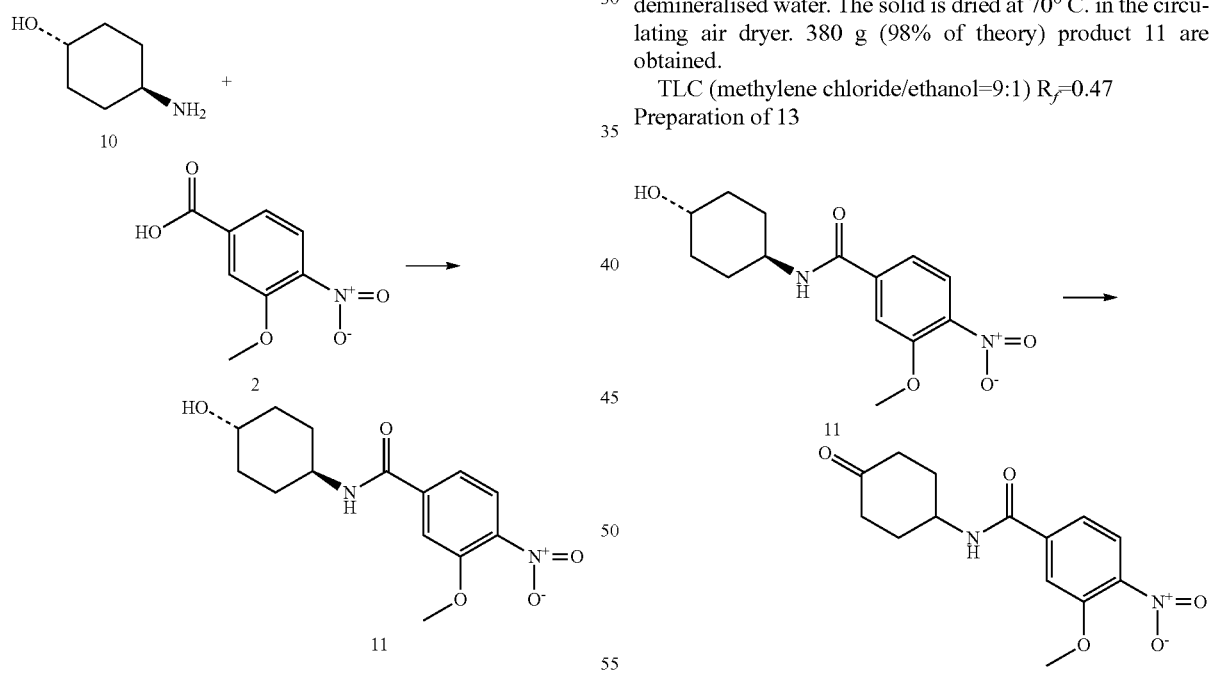

260 g (1.32 mol) 3-methoxy-4-nitrobenzoic acid 2 are placed in 1.5 L toluene. 300 mL toluene are distilled off. 5 mL dimethylformamide are added to the residue and 123 mL (1.7 mol) thionyl chloride are added dropwise thereto. The reaction solution is refluxed for 2 hours. The solvent is concentrated by evaporation using the rotary evaporator under reduced pressure. The residue is dissolved in 500 mL tetrahydrofuran and added dropwise to a suspension of 202 g (1.33 mol) trans-4-aminocyclohexanol 10 in 1.5 L tetrahydrofuran and 1.38 L of a 30% potassium carbonate solution, so that the temperature is maintained between 5° and 13° C. The mixture is stirred for 1 hour at 20° C. and 5 L demineralised water are added. The precipitate is suction filtered and washed with demineralised water. The solid is dried at 70° C. in the circulating air dryer. 380 g (98% of theory) product 11 are obtained.

TLC (methylene chloride/ethanol=9:1) $R_f$=0.47

Preparation of 13

1 g of finely powdered ruthenium(III)-chloride hydrate are added to 185 g (0.63 mol) 11 and 234 g N-methylmorpholine-N-oxide in 1.8 L acetonitrile and the mixture is refluxed for 1 hour. Under reduced pressure 1.6 L acetonitrile are evaporated off. 1.5 L demineralised water are added to the residue and the suspension is cooled to 5° C. The precipitate is suction filtered and washed with plenty of demineralised water. The solid is dried at 70° C. in the circulating air dryer. 168 g (91% of theory) product 13 are obtained.

TLC (methylene chloride/ethanol=9:1) $R_f$=0.64

Preparation of 14a

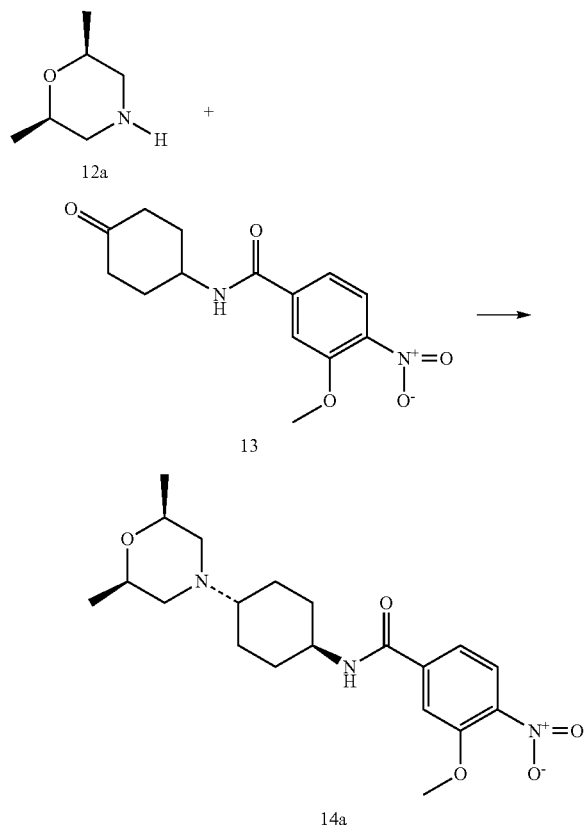

164 g (0.51 mol) 13 (90%), 80.1 mL (0.65 mol) cis-2,6-dimethylmorpholine 12 and 60 g sodium acetate in 1.4 L tetrahydrofuran are refluxed for 1 hour. The mixture is cooled to 20° C. and 120 g (0.57 mol) sodium triacetoxyborohydride are added batchwise in such a way that the temperature is kept between 18° and 22° C. The mixture is stirred for 16 hours at 20° C. The solvent is concentrated by evaporation under reduced pressure. The residue is dissolved in 2 normal hydrochloric acid. 10 g activated charcoal are added to the solution and it is suction filtered. 300 mL diisopropylether and then ammonia solution are added to the filtrate until the aqueous phase is alkaline. The mixture is stirred for one hour and the suspension is cooled to 5° C. The suspension is suction filtered and the solid is washed with demineralised water. The crude product is crystallised from 1.2 L isopropanol. The suction filtered crystalline product is dried at 50° C. in the circulating air dryer. 84 g (43% of theory) compound 14a are obtained.

TLC (methylene chloride/ethanol=9:1) $R_f$=0.45

Preparation of 14b

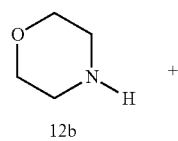

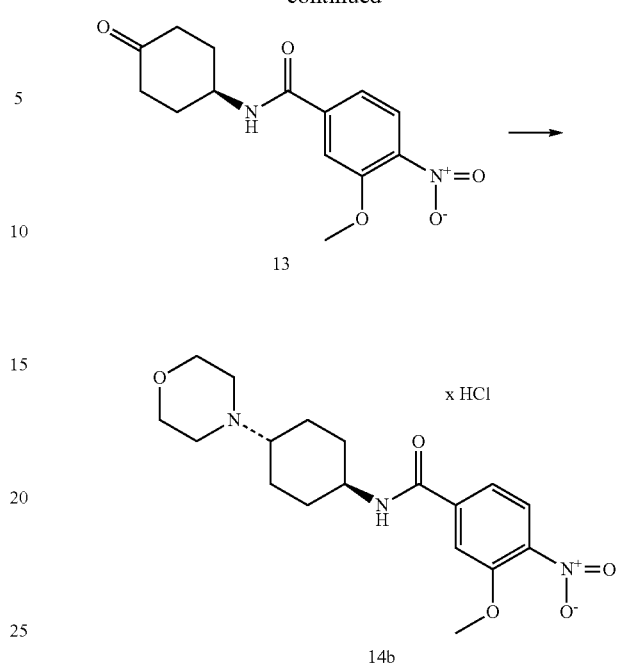

A suspension of 65.3 g (223 mmol) 13, 23.6 mL (268 mmol) morpholine 12b and 0.4 mL methanesulphonic acid in 600 mL toluene is refluxed using the water separator until total enamine formation is achieved. The solvent is distilled off under reduced pressure to leave a residual volume of 100 mL. The residue is dissolved with 400 mL ethanol at 80° C. and cooled to 0° to 5° C. At this temperature 10.1 g sodium borohyride are added batchwise and the mixture is then stirred for 16 hours at 20° C. Ice is added to the solution and it is adjusted to pH=8 to 9 by the addition of semiconcentrated hydrochloric acid. The solvents are concentrated by evaporation under reduced pressure. The residue is suspended in methylene chloride and chromatographed on silica gel with a solvent mixture of methylene chloride/ethanol/ammonia (49:1:0.25 to 19:1:0.25). First, the cis compound [TLC (methylene chloride/ethanol/ammonia=19:1:0.25) $R_f$=0.23] is eluted. Fractions containing the trans compound [TLC (methylene chloride/ethanol/ammonia=19:1:0.25) $R_f$=0.12] are combined and concentrated by evaporation. The residue is suspended in 350 mL methanol at boiling temperature. At approx. 50° C., 2 molar equivalents of trimethylchlorosilane are added followed by 500 mL tert.-butylmethylether. The suspension is suction filtered and the solid is dried.

24 g (27% of theory) compound 14b are obtained as the hydrochloride.

TLC (methylene chloride/ethanol/ammonia=19:1:0.25) $R_f$=0.12

Preparation of 14c

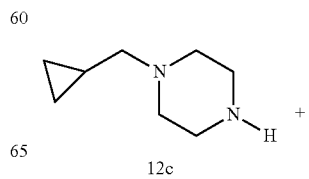

-continued

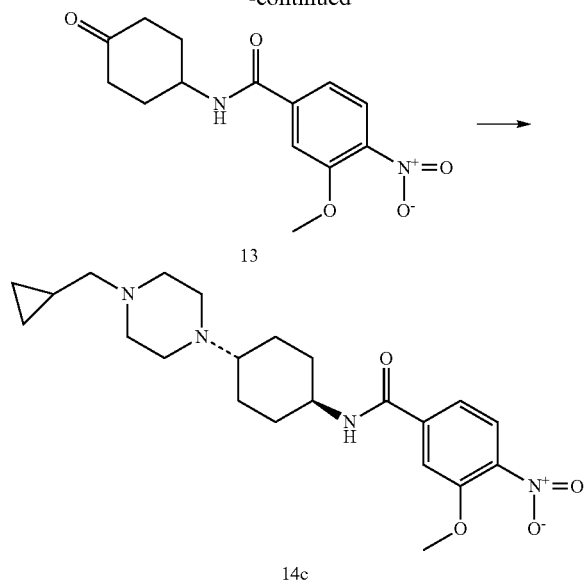

13

14c 112 g (383 mmol) 13, 108 g (770 mmol) N-(cyclopropylmethyl)piperazine 12c and 4.5 mL methanesulphonic acid in toluene are refluxed for 3 hours using the water separator (approx. 76 mL water are separated off). Under reduced pressure 900 mL toluene are evaporated off and the residue is suspended in 1.2 L ethanol. 15 g sodium borohydride are added batchwise to this suspension at a temperature of 15° to 25° C. within one hour. The mixture is stirred for 3 hours at 20° C. and another 4 g sodium borohydride are added. The mixture is stirred for 16 hours at 20° C. Under reduced pressure 650 mL ethanol are evaporated off. 2 L purified water and 300 mL cyclohexane are added. The mixture is cooled to 5° C. and the suspension is suction filtered. The residue is dissolved in 1 normal hydrochloric acid. 5 g activated charcoal are added and the mixture is suction filtered. 400 mL tert.-butylmethylether are added to the filtrate and it is made alkaline with ammonia solution. It is cooled to 4° C., the precipitate is suction filtered and washed with demineralised water. The residue is refluxed in 400 mL tert.-butylmethylether. It is cooled, the solid is suction filtered and washed with tert.-butylmethylether. After drying in the circulating air dryer at 60° C. 73 g (46% of theory) product 14c is obtained.

TLC (methylene chloride/ethanol=9:1) $R_f$=0.2
Preparation of 15a

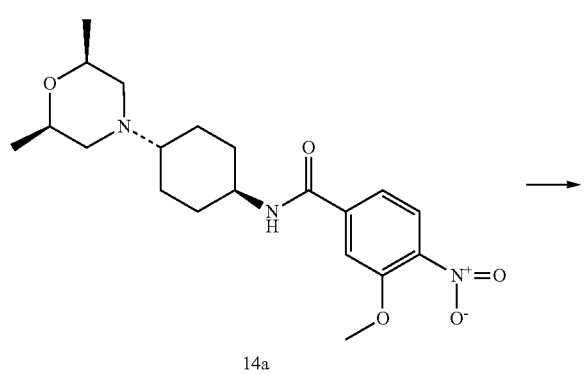

14a

-continued

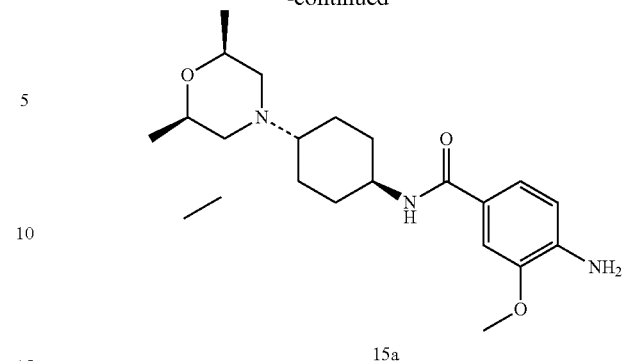

15a

A solution of 108.5 g (277 mmol) 14a in 900 mL acetic acid is hydrogenated in the presence of 10 g Raney nickel at a temperature of 20° C. and a hydrogen pressure of 50 psi. The catalyst is filtered off and the solution is concentrated by evaporation under reduced pressure. The residue is dissolved in 500 mL isopropanol and made alkaline by the addition of ammonia solution. Sufficient ice water is added to obtain a volume of 1.5 L. The precipitate is suction filtered and washed with 400 mL demineralised water, 160 mL isopropanol and 300 mL tert.-butylmethylether. The solid is dried at 50° C. in the circulating air dryer. 92 g (92% of theory) product 15a are obtained.

TLC (methylene chloride/ethanol=9:1) $R_f$=0.25
Preparation of 15b

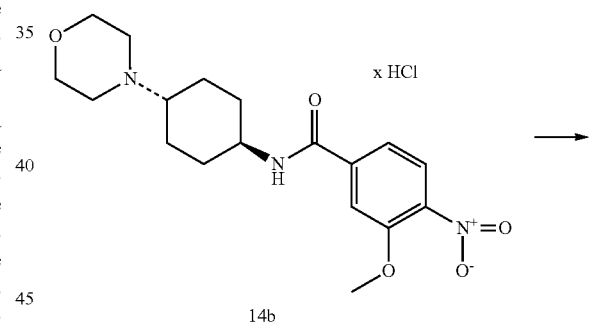

14b

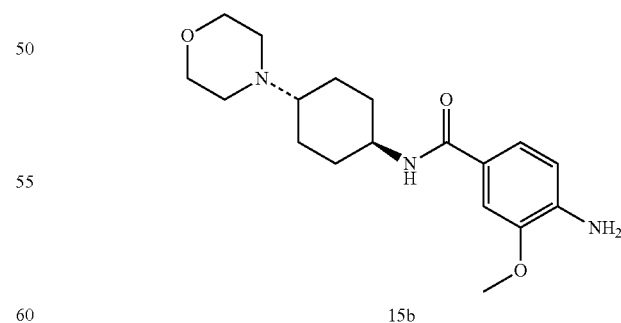

15b

A solution of 23 g (57.5 mmol) 14b hydrochloride in 200 mL demineralised water is hydrogenated in the presence of 5 g palladium on charcoal (10%) at a temperature of 20° C. and a hydrogen pressure of 50 psi. The catalyst is filtered off and the filtrate is slowly adjusted to pH=11 by the addition of 1 normal sodium hydroxide solution. The suspension is stirred for 2 hours at 20° C., suction filtered and the solid is washed with demineralised water. After drying in the vacuum drying cupboard 17.5 g product 15b is obtained.

Preparation of 15c

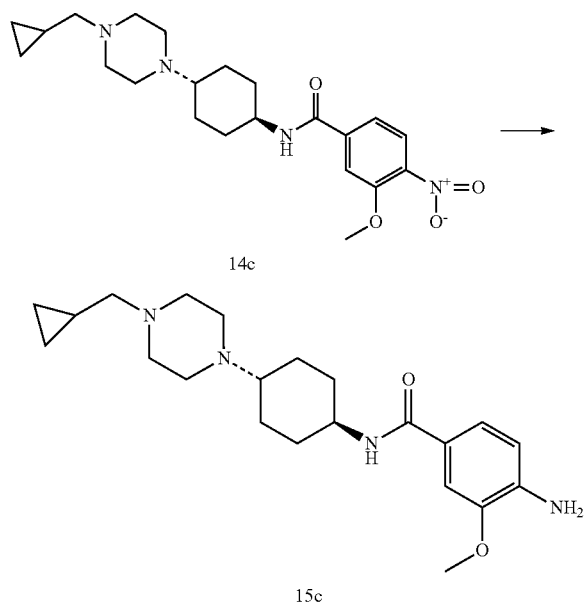

A solution of 72.5 g (174 mmol) 14c in 700 mL methanol and 145 mL dimethylformamide is hydrogenated in the presence of 10 g Raney nickel at a temperature of 20° C. and a hydrogen pressure of 50 psi. The catalyst is filtered off and the methanol is evaporated down under reduced pressure. 500 mL demineralised water are added to the residue and the suspension is cooled to 5° C. The precipitate is suction filtered and washed with demineralised water. After drying in the circulating air dryer at 60° C., 60.5 g (90% of theory) product 15c is obtained.

TLC (methylene chloride/ethanol/ammonia=9:1:0.1) $R_f$=0.58

Preparation of 17a (Corresponds to the Compound of Example No. 234)

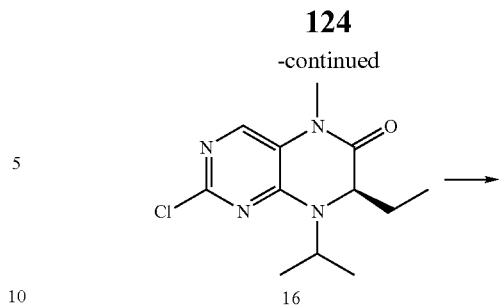

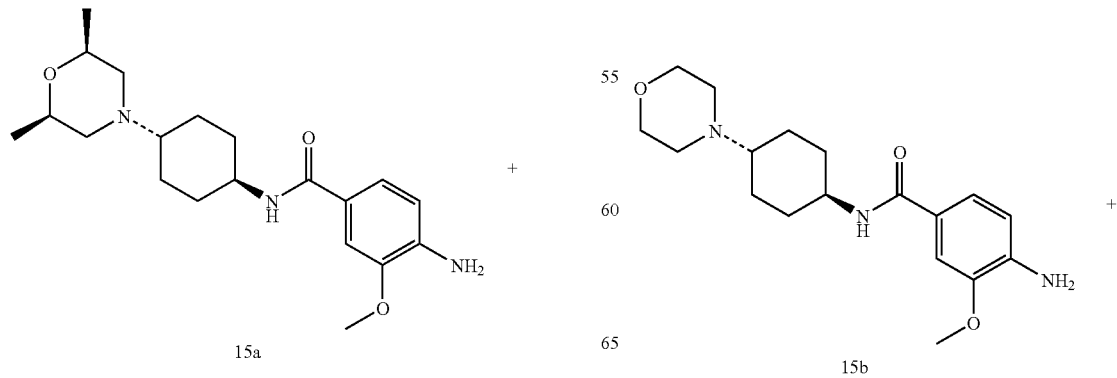

A solution of 20.2 g (55.9 mmol) 15a, 16.5 g (61.4 mmol) 16 and 15.9 g (83.6 mmol) para-toluenesulphonic acid hydrate in 400 mL 2-methyl-4-pentanol is refluxed for 9 hours, while a total of 360 mL solvent are distilled off over the entire period. The residue is left to cool and the solidified oil is dissolved in 300 mL demineralised water. The aqueous phase is washed three times with ethyl acetate. 400 mL ethyl acetate are added to the aqueous phase and sufficient sodium hydroxide solution is added to give a pH=11 to 12. The organic phase is washed twice with demineralised water. The organic phase is dried over sodium sulphate, filtered and the solvent is evaporated off under reduced pressure. The residue is dissolved in 82 mL dimethylacetamide and slowly added dropwise to a solution of 60 mL conc. ammonia in 1.4 L demineralised water with thorough stirring. The mixture is stirred for 4 hours at 20° C., the precipitate is suction filtered and washed with plenty of demineralised water. After drying at 60° C. in the vacuum drying cupboard in the presence of sodium hydroxide flakes 30.3 g product 17a is obtained.

The base thus obtained may be crystallised from acetone/1 normal hydrochloric acid as the monohydrochloride with an m.p. of approx. 320° C. (decomposition, DSC: 10 K/min).

Preparation of 17b (Corresponds to the Compound of Example No. 27)

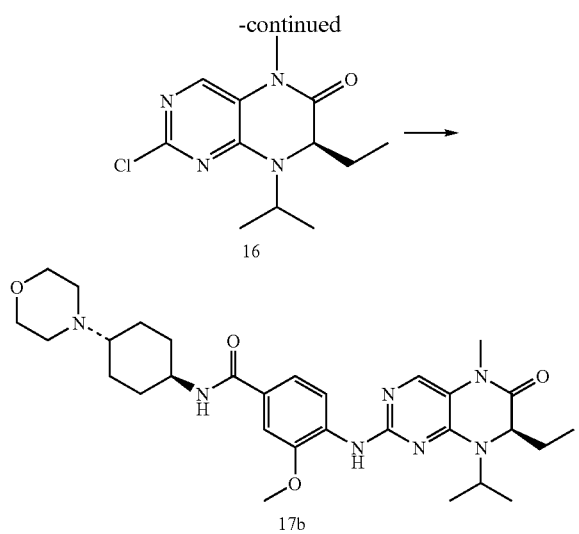

A solution of 16.2 g (48.6 mmol) 15b, 14.5 g (54 mmol) 16 and 13 g (68.3 mmol) para-toluenesulphonic acid hydrate in 250 mL 2-methyl-4-pentanol and 20 mL N-methylpyrrolidinone is refluxed. Within one hour 180 mL solvent are distilled off 100 mL 2-methyl-4-pentanol are added and the solution is refluxed for 5 hours. It is left to cool to 80° C. and 40 mL methanol and 12 g trimethylsilyl chloride are added. At 60° C., 400 mL of acetone are allowed to flow in. The suspension is refluxed and cooled to 30° C. The precipitate is suction filtered and washed with acetone/methanol (85:15) and acetone. After drying in the vacuum drying cupboard at 50° C., 22.7 g (78% of theory) product 17b is obtained as the hydrochloride.

After dissolving the hydrochloride in demineralised water and transferring it into an aqueous solution of potassium carbonate and common salt the free base is extracted with methylene chloride. The base of 17b is crystallised from acetone/demineralised:water (1:1) (m.p.=150° C., DSC: 10 K/min).

Preparation of 17c (Corresponds to the Compound of Example No. 110)

A solution of 23 g (59.5 mmol) 15c, 16.8 g (62.5 mmol) 16 and 28.3 g (149 mmol) para-toluenesulphonic acid hydrate in 350 mL 2-methyl-4-pentanol is refluxed for 22 hours using the water separator. After the addition of 1 g of 16 the mixture is refluxed for a further 2 hours. 300 mL solvent are distilled off and the viscous oil is allowed to cool to 60° C. 300 mL methylene chloride and 300 mL demineralised water are added and the pH is raised by adding approx. 20 mL of 10 normal sodium hydroxide solution to pH=9. The organic phase is washed twice with demineralised water and dried over sodium sulphate. The solvent is evaporated off under reduced pressure and the residue is dissolved at 65° C. in 200 mL ethyl acetate. The mixture is left to cool slowly to 20° C., the precipitate is suction filtered and washed with cold ethyl acetate. After drying at 60° C. in the vacuum drying cupboard 24.4 g product 17c is obtained (m.p.=182° C., DSC: 10 K/min, additional endothermic effects in the DSC diagram before melting).

The compound 14c may alternatively also be prepared by the following method (synthesis diagram 3).

Synthesis plan 3

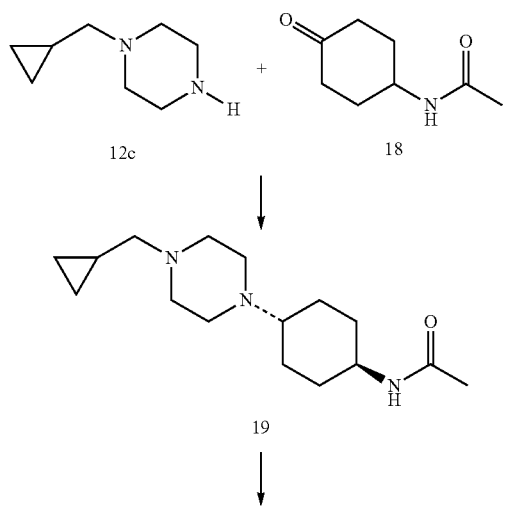

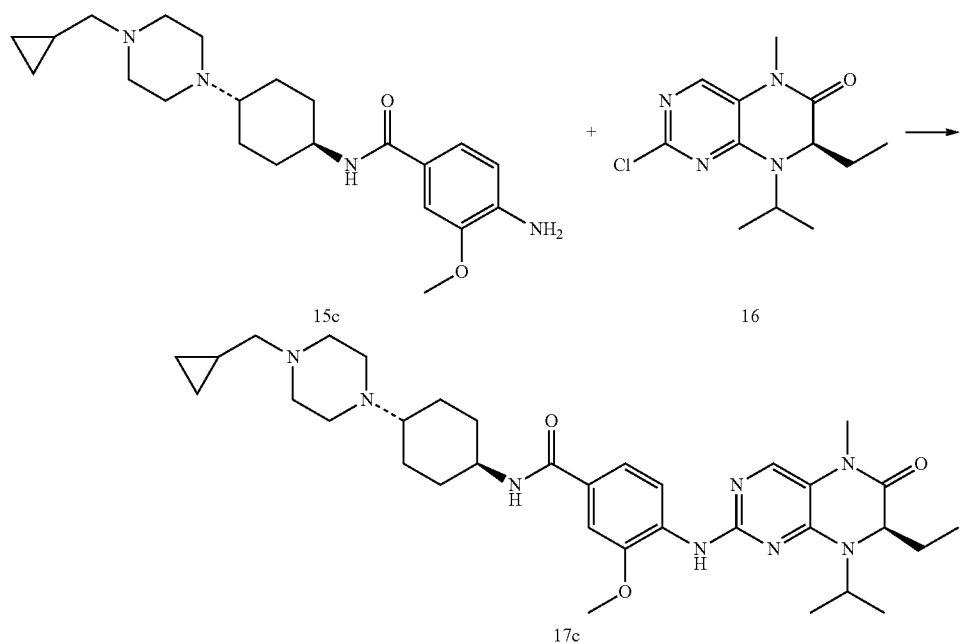

-continued

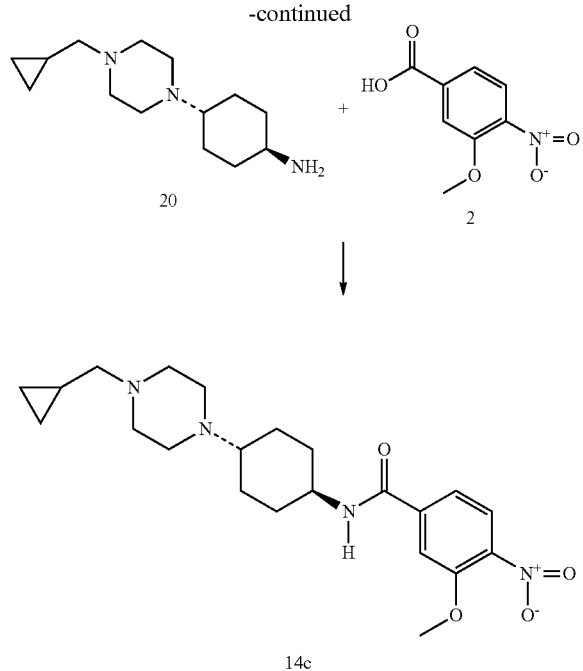

Preparation of 19

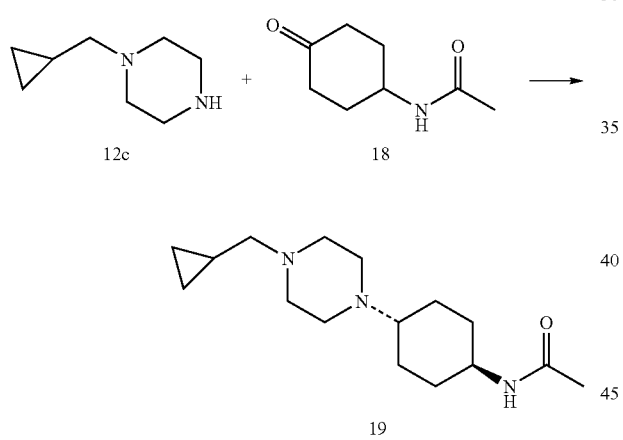

22 g (142 mmol) 4-acetamido-cyclohexanone 18, 39.7 g (283 mmol) N-cyclopropylmethylpiperazine 12c and 0.71 mL methanesulphonic acid in 175 mL toluene are refluxed using the water separator until no more water is precipitated. The mixture is left to cool and at 50° C. 175 mL ethanol are added and the resulting mixture is cooled to 20° C. 5.37 g (142 mmol) sodium borohydride are added batchwise with thorough stirring and the mixture is stirred for 16 hours at 20° C. 200 mL of 4 normal hydrochloric acid are added dropwise to the reaction mixture. Under reduced pressure 200 mL solvent are evaporated off. 100 mL saturated potassium carbonate solution and 200 mL methylisobutylketone are added to the residue. The two-phase mixture is cooled to 5° C. with thorough stirring. The product is suction filtered and dissolved at reflux temperature in 90 mL methylisobutylketone. After the addition of activated charcoal it is filtered hot. The mixture is left to cool and the precipitate is removed by suction filtering.

After drying, 16.2 g (41% of theory) of trans compound 12 are obtained TLC (methylene chloride/ethanol/ammonia=9:1:0.1) $R_f$=0.39

Preparation of 20

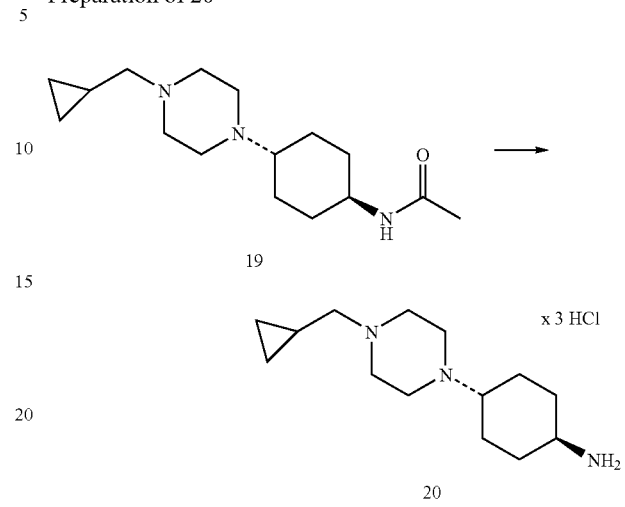

A solution of 44 g (157 mmol) 19 in 500 mL 24% hydrochloric acid is refluxed for 6 hours. The solvent is concentrated by evaporation under reduced pressure and the residue is crystallised from 700 mL isopropanol. The precipitate is suction filtered, washed with tert.-butylmethylether and dried at 60° C. in the vacuum drying cupboard. 54.7 g product 20 are obtained as the trihydrochloride (contains 5% water).

Preparation of 14c

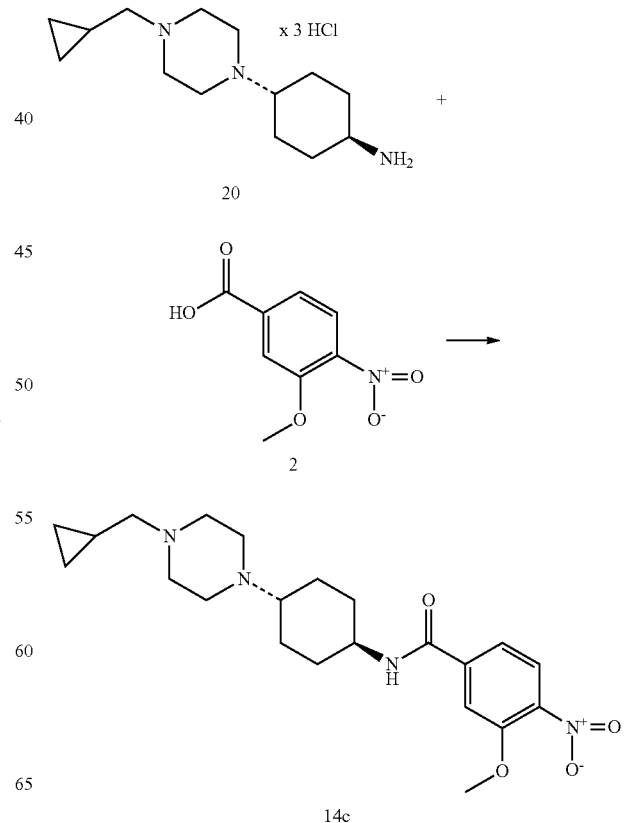

33 g (90.4 mmol) 3-methoxy-4-nitrobenzoic acid 2, are suspended in 80 mL toluene. 0.5 mL dimethylformamide and 16 g (134 mmol) thionyl chloride are added. The mixture is refluxed for 1 hour. The solution is concentrated by evaporation under reduced pressure and the crude acid chloride is dissolved in 50 mL tetrahydrofuran. The solution is added dropwise to a suspension of 18.7 g (94.9 mmol, 95%) of 20 trihydrochloride and 49 g (397 mmol) of diisopropylethylamine in 150 mL tetrahydrofuran while being cooled in the ice bath. TLC is used to check that the reaction is complete. After the reaction has ended water is added to the suspension and the pH is adjusted to 10 by the addition of sodium hydroxide solution. The organic phase is separated off and washed with saturated saline solution. The combined aqueous phases are extracted once with tetrahydrofuran. The combined organic phases are concentrated by evaporation under reduced pressure. The residue is refluxed in 300 mL tert.-butylmethylether. The mixture is left to cool to 20° C. and the precipitate is suction filtered. After drying in the vacuum drying cupboard at 45° C. 31.3 g (83% of theory) 14c is obtained.

The invention claimed is:

1. A Compound of formula

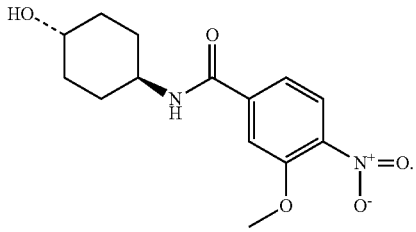

2. A Compound of formula

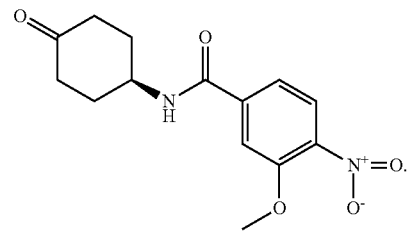

* * * * *